United States Patent
Keating et al.

(10) Patent No.: US 11,759,217 B2
(45) Date of Patent: Sep. 19, 2023

(54) CATHETER TUBULAR SUPPORT

(71) Applicant: Neuravi Limited, Galway (IE)

(72) Inventors: Karl Keating, Galway (IE); Ronald Kelly, Galway (IE); David Vale, Galway (IE)

(73) Assignee: Neuravi Limited, Galway (IE)

( * ) Notice: Subject to any disclaimer, the term of this patent is extended or adjusted under 35 U.S.C. 154(b) by 394 days.

(21) Appl. No.: 16/842,502

(22) Filed: Apr. 7, 2020

(65) Prior Publication Data

US 2021/0307766 A1    Oct. 7, 2021

(51) Int. Cl.
*A61B 17/22* (2006.01)
*A61B 17/00* (2006.01)

(52) U.S. Cl.
CPC .... *A61B 17/22* (2013.01); *A61B 2017/00867* (2013.01); *A61B 2017/22079* (2013.01)

(58) Field of Classification Search
CPC .......... A61B 17/22; A61B 2017/00309; A61B 17/3207; A61B 2017/00292; A61M 25/005; A61M 25/0051; A61M 25/0053; A61M 25/0054
See application file for complete search history.

(56) References Cited

U.S. PATENT DOCUMENTS

| | | |
|---|---|---|
| 4,243,040 A | 1/1981 | Beecher |
| 4,324,262 A | 4/1982 | Hall |
| 4,351,342 A | 9/1982 | Wiita et al. |
| 4,575,371 A | 3/1986 | Nordqvist et al. |
| 4,592,356 A | 6/1986 | Gutierrez |
| 4,719,924 A | 1/1988 | Crittenden et al. |
| 4,738,666 A | 4/1988 | Fuqua |
| 4,767,404 A | 8/1988 | Renton |
| 4,793,348 A | 12/1988 | Palmaz |

(Continued)

FOREIGN PATENT DOCUMENTS

| | | |
|---|---|---|
| CN | 1658920 A | 8/2005 |
| CN | 1972728 A | 5/2007 |

(Continued)

OTHER PUBLICATIONS

US 6,348,062 B1, 02/2002, Hopkins (withdrawn)

(Continued)

*Primary Examiner* — Julian W Woo
(74) *Attorney, Agent, or Firm* — TROUTMAN PEPPER HAMILTON SANDERS LLP

(57) ABSTRACT

A clot retrieval catheter can have a tailored, highly flexible body section capable of navigating tortuous routes and an expandable tip for local flow restriction/arrest. The body can be a support tube of struts with a plurality of ribs and one or more axial spines. The support tube can also be a tubular section with a pattern of radial slots to increase flexibility while inhibiting kinking and binding. The ribs and spines can have strut widths which vary along the length of the support tube or can have curves with a non-planar cross section. The ribs can be formed such that they can move when subjected to the loads of a thrombectomy procedure. The structure of the support tube can also be a braided or woven pattern of strands. The support tube can also have a polymer jacket or membrane disposed around at least a portion of the structure.

11 Claims, 22 Drawing Sheets

(56) References Cited

U.S. PATENT DOCUMENTS

| | | |
|---|---|---|
| 4,873,978 A | 10/1989 | Ginsburg |
| 5,011,488 A | 4/1991 | Ginsburg |
| 5,092,839 A | 3/1992 | Kipperman |
| 5,102,415 A | 4/1992 | Guenther et al. |
| 5,122,136 A | 6/1992 | Guglielmi et al. |
| 5,123,840 A | 6/1992 | Nates |
| 5,171,233 A | 12/1992 | Amplatz |
| 5,234,437 A | 8/1993 | Sepetka |
| 5,256,144 A | 10/1993 | Kraus et al. |
| 5,261,916 A | 11/1993 | Engelson |
| 5,372,124 A | 12/1994 | Takayama et al. |
| 5,385,562 A | 1/1995 | Adams |
| 5,387,219 A | 2/1995 | Rappe |
| 5,387,226 A | 2/1995 | Miraki |
| 5,396,902 A | 3/1995 | Brennen et al. |
| 5,449,372 A | 9/1995 | Schmaltz |
| 5,520,651 A | 5/1996 | Sutcu |
| 5,538,512 A | 7/1996 | Zenzon et al. |
| 5,549,626 A | 8/1996 | Miller et al. |
| 5,558,652 A | 9/1996 | Henke |
| 5,601,600 A | 2/1997 | Ton |
| 5,609,627 A | 3/1997 | Goicoechea et al. |
| 5,624,461 A | 4/1997 | Mariant |
| 5,639,277 A | 6/1997 | Mariant |
| 5,645,558 A | 7/1997 | Horton |
| 5,658,296 A | 8/1997 | Bates |
| 5,662,671 A | 9/1997 | Barbut |
| 5,695,519 A | 12/1997 | Summer et al. |
| 5,709,704 A | 1/1998 | Nott et al. |
| 5,713,853 A | 2/1998 | Clark |
| 5,728,078 A | 3/1998 | Powers, Jr. |
| 5,769,871 A | 6/1998 | Mers Kelly |
| 5,779,716 A | 7/1998 | Cano |
| 5,810,874 A | 9/1998 | Lefebvre |
| 5,814,064 A | 9/1998 | Danniel et al. |
| 5,827,304 A | 10/1998 | Hart |
| 5,846,251 A | 12/1998 | Hart |
| 5,855,598 A | 1/1999 | Pinchuk |
| 5,893,869 A | 4/1999 | Barnhart et al. |
| 5,895,398 A | 4/1999 | Wensel |
| 5,897,567 A | 4/1999 | Ressemann |
| 5,904,698 A | 5/1999 | Thomas et al. |
| 5,911,725 A | 6/1999 | Boury |
| 5,935,139 A | 8/1999 | Bates |
| 5,938,645 A | 8/1999 | Gordon |
| 5,947,995 A | 9/1999 | Samuels |
| 5,968,057 A | 10/1999 | Taheri |
| 5,971,938 A | 10/1999 | Hart et al. |
| 5,997,939 A | 12/1999 | Moechnig et al. |
| 6,022,343 A * | 2/2000 | Johnson ............... F16L 11/081 604/524 |
| 6,063,113 A | 5/2000 | Kavteladze |
| 6,066,149 A | 5/2000 | Samson et al. |
| 6,066,158 A | 5/2000 | Engelson |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates |
| 6,102,932 A | 8/2000 | Kurz |
| 6,106,548 A | 8/2000 | Roubin et al. |
| 6,129,739 A | 10/2000 | Khosravi |
| 6,142,957 A | 11/2000 | Diamond et al. |
| 6,146,396 A | 11/2000 | Kónya et al. |
| 6,146,404 A | 11/2000 | Kim |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi |
| 6,203,561 B1 | 3/2001 | Ramee |
| 6,214,026 B1 | 4/2001 | Lepak |
| 6,221,006 B1 | 4/2001 | Dubrul |
| 6,238,412 B1 | 5/2001 | Dubrul |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,306,163 B1 | 10/2001 | Fitz |
| 6,309,379 B1 | 10/2001 | Willard |
| 6,312,444 B1 | 11/2001 | Barbut |
| 6,315,778 B1 | 11/2001 | Gambale et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,348,056 B1 | 2/2002 | Bates |
| 6,350,271 B1 | 2/2002 | Kurz et al. |
| 6,361,545 B1 | 3/2002 | Macoviak |
| 6,371,963 B1 | 4/2002 | Nishtala et al. |
| 6,375,668 B1 | 4/2002 | Gifford et al. |
| 6,383,205 B1 | 5/2002 | Samson et al. |
| 6,383,206 B1 | 5/2002 | Gillick |
| 6,391,037 B1 | 5/2002 | Greenhalgh |
| 6,402,771 B1 | 6/2002 | Palmer |
| 6,409,683 B1 | 6/2002 | Fonseca et al. |
| 6,416,541 B2 | 7/2002 | Denardo |
| 6,425,909 B1 | 7/2002 | Dieck et al. |
| 6,432,122 B1 | 8/2002 | Gilson et al. |
| 6,436,112 B2 | 8/2002 | Wensel |
| 6,458,139 B1 | 10/2002 | Palmer |
| 6,346,116 B1 | 11/2002 | Brooks et al. |
| 6,485,497 B2 | 11/2002 | Wensel |
| 6,485,501 B1 | 11/2002 | Green |
| 6,485,502 B2 | 11/2002 | Don Michael |
| 6,511,492 B1 | 1/2003 | Rosenbluth |
| 6,517,551 B1 | 2/2003 | Driskill |
| 6,520,934 B1 | 2/2003 | Lee et al. |
| 6,520,951 B1 | 2/2003 | Carrillo, Jr. |
| 6,530,935 B2 | 3/2003 | Wensel |
| 6,530,939 B1 | 3/2003 | Hopkins |
| 6,540,768 B1 | 4/2003 | Diaz et al. |
| 6,544,279 B1 | 4/2003 | Hopkins |
| 6,551,341 B2 | 4/2003 | Boylan et al. |
| 6,551,342 B1 | 4/2003 | Shen et al. |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,616 B1 | 7/2003 | Stack |
| 6,602,271 B2 | 8/2003 | Adams |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi |
| 6,632,241 B1 | 10/2003 | Hanoock et al. |
| 6,638,245 B2 | 10/2003 | Miller |
| 6,638,293 B1 | 10/2003 | Makower et al. |
| 6,641,590 B1 | 11/2003 | Palmer et al. |
| 6,652,555 B1 | 11/2003 | VanTassel et al. |
| 6,656,218 B1 | 12/2003 | Denardo et al. |
| 6,660,021 B1 | 12/2003 | Palmer et al. |
| 6,663,650 B2 | 12/2003 | Sepetka |
| 6,673,089 B1 | 1/2004 | Yassour et al. |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,702,782 B2 | 3/2004 | Miller |
| 6,712,834 B2 | 3/2004 | Yassour et al. |
| 6,726,701 B2 | 4/2004 | Gilson et al. |
| 6,730,104 B1 | 5/2004 | Sepetka |
| 6,726,703 B2 | 8/2004 | Broome et al. |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |
| 6,913,618 B2 | 7/2005 | Denardo et al. |
| 6,953,472 B2 | 10/2005 | Palmer et al. |
| 6,989,019 B2 | 1/2006 | Mazzocchi |
| 6,989,021 B2 | 1/2006 | Bosma et al. |
| 6,994,718 B2 | 2/2006 | Groothuis et al. |
| 6,997,939 B2 | 2/2006 | Linder |

(56) References Cited

U.S. PATENT DOCUMENTS

| | | |
|---|---|---|
| 7,004,954 B1 | 2/2006 | Voss et al. |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukernik |
| 7,041,116 B2 | 5/2006 | Goto |
| 7,048,758 B2 | 5/2006 | Boyle |
| 7,058,456 B2 | 6/2006 | Pierce |
| 7,063,707 B2 | 6/2006 | Bose |
| 7,153,320 B2 | 12/2006 | Euteneuer et al. |
| 7,175,655 B1 | 2/2007 | Malaei |
| 7,179,273 B1 | 2/2007 | Palmer et al. |
| 7,220,269 B1 | 5/2007 | Ansel |
| 7,220,271 B2 | 5/2007 | Clubb |
| 7,226,464 B2 | 6/2007 | Garner et al. |
| 7,229,472 B2 | 6/2007 | DePalma et al. |
| 7,232,462 B2 | 6/2007 | Schaeffer |
| 7,288,112 B2 | 10/2007 | Denardo et al. |
| 7,306,618 B2 | 12/2007 | Demond |
| 7,316,692 B2 | 1/2008 | Huffmaster |
| 7,323,001 B2 | 1/2008 | Cubb |
| 7,331,976 B2 | 2/2008 | McGuckin, Jr. et al. |
| 7,344,550 B2 | 3/2008 | Garrison et al. |
| 7,399,308 B2 | 7/2008 | Borillo et al. |
| 7,410,491 B2 | 8/2008 | Hopkins |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik et al. |
| 7,594,926 B2 | 9/2009 | Linder |
| 7,604,649 B2 | 10/2009 | McGuckin et al. |
| 7,618,434 B2 | 11/2009 | Santra et al. |
| 7,662,165 B2 | 2/2010 | Gilson et al. |
| 7,670,356 B2 | 3/2010 | Mazzocchi |
| 7,691,121 B2 | 4/2010 | Rosenbluth |
| 7,691,124 B2 | 4/2010 | Balgobin |
| 7,708,770 B2 | 5/2010 | Linder |
| 7,736,385 B2 | 6/2010 | Agnew |
| 7,766,934 B2 | 8/2010 | Pal |
| 7,771,452 B2 | 8/2010 | Pal |
| 7,780,694 B2 | 8/2010 | Palmer |
| 7,780,696 B2 | 8/2010 | Daniel et al. |
| 7,819,893 B2 | 10/2010 | Brady et al. |
| 7,828,815 B2 | 11/2010 | Mazzocchi |
| 7,846,176 B2 | 11/2010 | Mazzocchi |
| 7,846,175 B2 | 12/2010 | Bonnette et al. |
| 7,850,708 B2 | 12/2010 | Pal |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,349 B2 | 4/2011 | Brady et al. |
| 7,927,784 B2 | 4/2011 | Simpson |
| 7,931,659 B2 | 4/2011 | Bose et al. |
| 3,002,822 A1 | 8/2011 | Glocker et al. |
| 7,998,165 B2 | 8/2011 | Huffmaster |
| 3,021,379 A1 | 9/2011 | Thompson et al. |
| 3,021,380 A1 | 9/2011 | Thompson et al. |
| 8,043,326 B2 | 10/2011 | Hancock et al. |
| 8,048,151 B2 | 11/2011 | O'Brien et al. |
| 8,052,640 B2 | 11/2011 | Fiorella et al. |
| 8,057,497 B1 | 11/2011 | Raju et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Garrison et al. |
| 8,123,769 B2 | 2/2012 | Osborne |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,357,178 B2 | 1/2013 | Grandfield et al. |
| 8,357,179 B2 | 1/2013 | Grandfield et al. |
| 8,357,893 B2 | 1/2013 | Xu et al. |
| 8,361,095 B2 | 1/2013 | Osborne |
| 8,366,663 B2 | 2/2013 | Fiorella et al. |
| 8,372,133 B2 | 2/2013 | Douk et al. |
| 8,382,742 B2 * | 2/2013 | Hermann ............ A61B 17/1631 606/1 |
| 8,409,215 B2 | 4/2013 | Sepetka et al. |
| 8,419,748 B2 | 4/2013 | Valaie |
| 8,460,312 B2 | 6/2013 | Bose et al. |
| 8,460,313 B2 * | 6/2013 | Huffmaster .......... A61B 17/221 606/127 |
| 8,486,104 B2 | 7/2013 | Samson et al. |
| 8,529,596 B2 | 9/2013 | Grandfield et al. |
| 8,574,262 B2 | 11/2013 | Ferrera et al. |
| 8,579,915 B2 | 11/2013 | French et al. |
| 8,585,643 B2 * | 11/2013 | Vo .................. A61M 25/0053 604/524 |
| 8,585,713 B2 | 11/2013 | Ferrera et al. |
| 8,608,761 B2 | 12/2013 | Osbourne et al. |
| 8,679,142 B2 | 3/2014 | Slee et al. |
| 8,696,622 B2 | 4/2014 | Fiorella et al. |
| 8,702,652 B2 | 4/2014 | Fiorella et al. |
| 8,702,724 B2 | 4/2014 | Olsen et al. |
| 8,784,434 B2 | 7/2014 | Rosenbluth et al. |
| 8,784,441 B2 | 7/2014 | Rosenbluth et al. |
| 8,795,305 B2 | 8/2014 | Grandfield et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,900,265 B1 | 12/2014 | Ulm, III |
| 8,939,991 B2 | 1/2015 | Krolick et al. |
| 8,945,143 B2 | 2/2015 | Ferrera et al. |
| 8,945,172 B2 | 2/2015 | Ferrera et al. |
| 8,968,330 B2 | 3/2015 | Rosenbluth et al. |
| 9,039,749 B2 | 5/2015 | Shrivastava et al. |
| 9,072,537 B2 | 7/2015 | Grandfield et al. |
| 9,113,936 B2 | 8/2015 | Palmer et al. |
| 9,119,656 B2 | 9/2015 | Bose et al. |
| 9,138,307 B2 | 9/2015 | Valaie |
| 9,149,609 B2 | 10/2015 | Ansel et al. |
| 9,155,552 B2 | 10/2015 | Ulm, III |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,221,132 B2 | 12/2015 | Bowman |
| 9,232,992 B2 | 1/2016 | Heidner |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,635 B2 | 5/2017 | Vale et al. |
| 9,642,675 B2 | 5/2017 | Werneth et al. |
| 9,655,633 B2 | 5/2017 | Leynov et al. |
| 9,655,645 B2 | 5/2017 | Staunton |

(56) References Cited

U.S. PATENT DOCUMENTS

| | | |
|---|---|---|
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Paterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,028,759 B2 | 7/2018 | Wallace et al. |
| 10,149,692 B2 | 12/2018 | Turjman et al. |
| 10,265,086 B2 | 4/2019 | Vale |
| 10,716,915 B2 | 7/2020 | Ogle et al. |
| 10,610,668 B2 | 8/2020 | Burkholz et al. |
| 10,835,271 B2 | 11/2020 | Ma |
| 2001/0001315 A1 | 5/2001 | Bates |
| 2001/0011182 A1 | 8/2001 | Dubrul et al. |
| 2001/0016755 A1 | 8/2001 | Addis |
| 2001/0041899 A1 | 11/2001 | Foster |
| 2001/0044598 A1 | 11/2001 | Parodi |
| 2001/0044634 A1 | 11/2001 | Don Michael et al. |
| 2001/0051810 A1 | 12/2001 | Dubrul |
| 2002/0002383 A1 | 1/2002 | Sepetka et al. |
| 2002/0016609 A1 | 2/2002 | Wensel |
| 2002/0022859 A1 | 2/2002 | Hogendijk |
| 2002/0026211 A1 | 2/2002 | Khosravi |
| 2002/0049468 A1 | 4/2002 | Streeter |
| 2002/0052620 A1 | 5/2002 | Barvut |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0143362 A1 | 10/2002 | Macoviak et al. |
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0177800 A1 | 11/2002 | Bagaoisan et al. |
| 2002/0188276 A1 | 12/2002 | Evans |
| 2003/0004536 A1 | 1/2003 | Boylan et al. |
| 2003/0004538 A1 | 1/2003 | Secrest |
| 2003/0004542 A1 | 1/2003 | Wensel |
| 2003/0009146 A1 | 1/2003 | Muni |
| 2003/0009191 A1 | 1/2003 | Wensel |
| 2003/0023204 A1 | 1/2003 | Vo et al. |
| 2003/0040769 A1 | 2/2003 | Kelley et al. |
| 2003/0040772 A1 | 2/2003 | Hyodoh et al. |
| 2003/0050663 A1 | 3/2003 | Khachin |
| 2003/0105484 A1 | 6/2003 | Boyle et al. |
| 2003/0125798 A1 | 7/2003 | Matrin |
| 2003/0130682 A1 | 7/2003 | Broome et al. |
| 2003/0144687 A1 | 7/2003 | Brady et al. |
| 2003/0153940 A1 | 8/2003 | Nohilly et al. |
| 2003/0153943 A1 | 8/2003 | Michael et al. |
| 2003/0153944 A1 | 8/2003 | Phung |
| 2003/0163064 A1 | 8/2003 | Vrba |
| 2003/0163158 A1 | 8/2003 | Wlite |
| 2003/0171769 A1 | 9/2003 | Barbut |
| 2003/0176884 A1 | 9/2003 | Berrada et al. |
| 2003/0187495 A1 | 10/2003 | Cully et al. |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0212430 A1 | 11/2003 | Bose |
| 2003/0216611 A1 | 11/2003 | Vu |
| 2003/0236533 A1 | 12/2003 | Wilson |
| 2004/0010280 A1 | 1/2004 | Adams et al. |
| 2004/0010282 A1 | 1/2004 | Kusleika |
| 2004/0014002 A1 | 1/2004 | Lundgren |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0093065 A1 | 5/2004 | Yachia et al. |
| 2004/0133231 A1 | 7/2004 | Maitland |
| 2004/0138692 A1 | 7/2004 | Phung |
| 2004/0153049 A1 | 8/2004 | Hewitt et al. |
| 2004/0153118 A1 | 8/2004 | Clubb |
| 2004/0193107 A1 | 9/2004 | Pierpont et al. |
| 2004/0199202 A1 | 10/2004 | Dubrul et al. |
| 2004/0260333 A1 | 12/2004 | Dubrul et al. |
| 2005/0015047 A1 | 1/2005 | Shah |
| 2005/0020974 A1 | 1/2005 | Noriega |
| 2005/0033348 A1 | 2/2005 | Sepetka |
| 2005/0038447 A1 | 2/2005 | Huffmaster |
| 2005/0038468 A1 | 2/2005 | Panetta et al. |
| 2005/0049619 A1 | 3/2005 | Sepetka |
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059993 A1 | 3/2005 | Ramzipoor et al. |
| 2005/0059995 A1 | 3/2005 | Sepetka |
| 2005/0085849 A1 | 4/2005 | Sepetka |
| 2005/0090857 A1 | 4/2005 | Kusleika et al. |
| 2005/0119668 A1 | 6/2005 | Teague et al. |
| 2005/0125024 A1 | 6/2005 | Sepetka |
| 2005/0149111 A1 | 7/2005 | Kanazawa et al. |
| 2005/0171566 A1 | 8/2005 | Kanamaru |
| 2005/0187570 A1 | 8/2005 | Nguyen et al. |
| 2005/0267491 A1 | 8/2005 | Kellett et al. |
| 2005/0216030 A1 | 9/2005 | Sepetka |
| 2005/0216050 A1 | 9/2005 | Sepetka |
| 2005/0288686 A1 | 9/2005 | Sepetka |
| 2005/0228417 A1 | 10/2005 | Teitelbaum et al. |
| 2006/0009785 A1 | 1/2006 | Maitland et al. |
| 2006/0009799 A1 | 1/2006 | Kleshinski et al. |
| 2006/0010636 A1 | 1/2006 | Vacher |
| 2006/0030933 A1 | 2/2006 | DeLeggge et al. |
| 2006/0036271 A1 | 2/2006 | Schomer et al. |
| 2006/0058836 A1 | 3/2006 | Bose |
| 2006/0058837 A1 | 3/2006 | Bose |
| 2006/0058838 A1 | 3/2006 | Bose |
| 2006/0064151 A1 | 3/2006 | Guterman et al. |
| 2006/0149313 A1 | 7/2006 | Arguello et al. |
| 2006/0155305 A1 | 7/2006 | Freudenthal |
| 2006/0155322 A1 | 7/2006 | Sater et al. |
| 2006/0161187 A1 | 7/2006 | Levine et al. |
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0282111 A1 | 12/2006 | Morsi |
| 2006/0287701 A1 | 12/2006 | Pal |
| 2007/0088383 A1 | 4/2007 | Pal et al. |
| 2007/0142858 A1 | 6/2007 | Bates |
| 2007/0149996 A1 | 6/2007 | Coughlin |
| 2007/0156170 A1 | 7/2007 | Hancock |

(56) References Cited

U.S. PATENT DOCUMENTS

| | | |
|---|---|---|
| 2007/0165170 A1 | 7/2007 | Fukuda |
| 2007/0191866 A1 | 8/2007 | Palmer et al. |
| 2007/0198028 A1 | 8/2007 | Miloslavski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0213765 A1 | 9/2007 | Adams et al. |
| 2007/0225749 A1 | 9/2007 | Martin |
| 2007/0239254 A1 | 10/2007 | Chia et al. |
| 2007/0244505 A1 | 10/2007 | Gilson et al. |
| 2007/0270902 A1 | 11/2007 | Slazas et al. |
| 2007/0288038 A1 | 12/2007 | Bimbo |
| 2007/0293887 A1 | 12/2007 | Okushi et al. |
| 2008/0045881 A1 | 2/2008 | Teitelbaum et al. |
| 2008/0082107 A1 | 4/2008 | Miller et al. |
| 2008/0086190 A1 | 4/2008 | Ta |
| 2008/0091223 A1 | 4/2008 | Pokorney |
| 2008/0097398 A1 | 4/2008 | Mitelberg |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0177296 A1 | 7/2008 | Sepetka |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0188928 A1 | 8/2008 | Salahieh |
| 2008/0200946 A1 | 8/2008 | Braun |
| 2008/0215077 A1 | 9/2008 | Sepetka |
| 2008/0221600 A1 | 9/2008 | Dieck et al. |
| 2008/0228209 A1 | 9/2008 | DeMello et al. |
| 2008/0234706 A1 | 9/2008 | Sepetka |
| 2008/0243170 A1 | 10/2008 | Jenson |
| 2008/0255596 A1 | 10/2008 | Jenson |
| 2008/0262528 A1 | 10/2008 | Martin |
| 2008/0262532 A1 | 10/2008 | Martin |
| 2008/0275488 A1 | 11/2008 | Fleming |
| 2008/0275493 A1 | 11/2008 | Farmiga |
| 2008/0281350 A1 | 11/2008 | Sepetka |
| 2008/0312681 A1 | 12/2008 | Ansel |
| 2009/0024157 A1 | 1/2009 | Anukhin |
| 2009/0054918 A1 | 2/2009 | Henson |
| 2009/0069828 A1 | 3/2009 | Martin |
| 2009/0076539 A1 | 3/2009 | Valaie |
| 2009/0105722 A1 | 4/2009 | Fulkerson |
| 2009/0105737 A1 | 4/2009 | Fulkerson |
| 2009/0131908 A1 | 5/2009 | McKay |
| 2009/0163846 A1 | 5/2009 | Aklog et al. |
| 2009/0177206 A1 | 7/2009 | Lozier et al. |
| 2009/0182336 A1 | 7/2009 | Brenzel et al. |
| 2009/0221967 A1 | 9/2009 | Thommen et al. |
| 2009/0270815 A1 | 10/2009 | Stamp et al. |
| 2009/0281610 A1 | 11/2009 | Parker |
| 2009/0292297 A1 | 11/2009 | Ferrere |
| 2009/0292307 A1 | 11/2009 | Razack |
| 2009/0299374 A1 | 12/2009 | Tilson et al. |
| 2009/0299393 A1 | 12/2009 | Martin |
| 2009/0306702 A1 | 12/2009 | Miloslavski |
| 2010/0004607 A1 | 1/2010 | Wilson et al. |
| 2010/0030186 A1 | 2/2010 | Stivland |
| 2010/0030256 A1 | 2/2010 | Dubrul et al. |
| 2010/0036312 A1 | 2/2010 | Krolik et al. |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0249815 A1 | 9/2010 | Jantzen et al. |
| 2010/0268264 A1 | 10/2010 | Bonnett et al. |
| 2010/0268265 A1 | 10/2010 | Krolik et al. |
| 2010/0292726 A1 | 11/2010 | Olsen et al. |
| 2010/0305566 A1 | 12/2010 | Rosenblatt et al. |
| 2010/0305604 A1 | 12/2010 | Pah |
| 2010/0318178 A1 | 12/2010 | Rapaport et al. |
| 2010/0324649 A1 | 12/2010 | Mattsson |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009942 A1 | 1/2011 | Gregorich |
| 2011/0022149 A1 | 1/2011 | Cox et al. |
| 2011/0054514 A1 | 3/2011 | Arcand |
| 2011/0054516 A1 | 3/2011 | Keegan |
| 2011/0060359 A1 | 3/2011 | Hannes |
| 2011/0071432 A1 | 3/2011 | Carrillo, Jr. et al. |
| 2011/0077620 A1 | 3/2011 | deBeer |
| 2011/0098683 A1 | 4/2011 | Wiita et al. |
| 2011/0054504 A1 | 5/2011 | Wolf et al. |
| 2011/0125181 A1 | 5/2011 | Brady et al. |
| 2011/0130756 A1 | 6/2011 | Everson, Jr. et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0196414 A1 | 8/2011 | Porter et al. |
| 2011/0202088 A1 | 8/2011 | Eckhouse et al. |
| 2011/0213290 A1 | 9/2011 | Chin et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0218564 A1 | 9/2011 | Drasler et al. |
| 2011/0224707 A1 | 9/2011 | Miloslavski et al. |
| 2011/0264132 A1 | 10/2011 | Strauss et al. |
| 2011/0276120 A1 | 11/2011 | Gilson et al. |
| 2011/0319917 A1 | 12/2011 | Ferrera et al. |
| 2012/0041449 A1 | 2/2012 | Eckhouse et al. |
| 2012/0041474 A1 | 2/2012 | Eckhouse et al. |
| 2012/0059356 A1 | 3/2012 | diPama et al. |
| 2012/0089216 A1 | 4/2012 | Rapaport et al. |
| 2012/0101510 A1 | 4/2012 | Lenker et al. |
| 2012/0116351 A1 | 5/2012 | Chomas et al. |
| 2012/0116440 A1 | 5/2012 | Leynov et al. |
| 2012/0143237 A1 | 6/2012 | Cam et al. |
| 2012/0143239 A1 | 6/2012 | Aklog et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2013/0006284 A1 | 1/2013 | Aggerholm et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144326 A1 | 6/2013 | Brady et al. |
| 2013/0144328 A1 | 6/2013 | Weber et al. |
| 2013/0158592 A1 | 6/2013 | Porter |
| 2013/0184703 A1 | 7/2013 | Shireman et al. |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0289697 A1 | 10/2013 | Baker et al. |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0012281 A1 | 1/2014 | Wang et al. |
| 2014/0046359 A1 | 2/2014 | Bowman et al. |
| 2014/0052097 A1 | 2/2014 | Petersen et al. |
| 2014/0081243 A1 | 3/2014 | Zhou et al. |
| 2014/0121672 A1 | 5/2014 | Folk |
| 2014/0128905 A1 | 5/2014 | Molaei |
| 2014/0135812 A1 | 5/2014 | Divino et al. |
| 2014/0180377 A1 | 6/2014 | Bose et al. |
| 2014/0188127 A1 | 7/2014 | Dubrul et al. |
| 2014/0194919 A1 | 7/2014 | Losardo et al. |
| 2014/0200607 A1 | 7/2014 | Sepetka et al. |

(56) References Cited

U.S. PATENT DOCUMENTS

| | | |
|---|---|---|
| 2014/0200608 A1 | 7/2014 | Brady et al. |
| 2014/0236220 A1 | 8/2014 | Inoue |
| 2014/0257018 A1 | 9/2014 | Farnan |
| 2014/0257362 A1 | 9/2014 | Eldenschink |
| 2014/0276922 A1 | 9/2014 | McLain et al. |
| 2014/0277003 A1 | 9/2014 | Hendrick |
| 2014/0277053 A1 | 9/2014 | Wang et al. |
| 2014/0277079 A1 | 9/2014 | Vale et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0364896 A1 | 12/2014 | Consigny |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0080937 A1 | 3/2015 | Davidson |
| 2015/0081003 A1 | 3/2015 | Wainwright et al. |
| 2015/0112376 A1 | 4/2015 | Molaei et al. |
| 2015/0133990 A1 | 5/2015 | Davidson |
| 2015/0142043 A1 | 5/2015 | Furey |
| 2015/0164523 A1 | 6/2015 | Brady et al. |
| 2015/0173783 A1 | 6/2015 | Tah et al. |
| 2015/0238314 A1 | 8/2015 | Börtlein et al. |
| 2015/0250497 A1 | 9/2015 | Marks et al. |
| 2015/0257775 A1 | 9/2015 | Gilvarry et al. |
| 2015/0258270 A1 | 9/2015 | Kunis |
| 2015/0297252 A1 | 10/2015 | Miloslavski et al. |
| 2015/0306311 A1 | 10/2015 | Pinchuk et al. |
| 2015/0313617 A1 | 11/2015 | Grandfield et al. |
| 2015/0320431 A1 | 11/2015 | Ulm, III |
| 2015/0351770 A1 | 12/2015 | Fulton, III |
| 2015/0352325 A1 | 12/2015 | Quick |
| 2015/0359547 A1 | 12/2015 | Vale et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0066921 A1 | 3/2016 | Brady et al. |
| 2016/0074067 A1 | 3/2016 | Furnish et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0121080 A1 | 5/2016 | Cottone |
| 2016/0135829 A1 | 5/2016 | Holochwost et al. |
| 2016/0143653 A1 | 5/2016 | Yale et al. |
| 2016/0151079 A1 | 6/2016 | Aklog et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0228134 A1 | 8/2016 | Martin et al. |
| 2016/0256180 A1 | 9/2016 | Vale et al. |
| 2016/0262880 A1 | 9/2016 | Li et al. |
| 2016/0317168 A1 | 11/2016 | Brady et al. |
| 2016/0346002 A1 | 12/2016 | Avneri et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0065401 A1 | 3/2017 | Fearnot et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095138 A1 | 4/2017 | Nakade et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172554 A1 | 6/2017 | Bortlein et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0238953 A1 | 8/2017 | Yang et al. |
| 2017/0252043 A1 | 9/2017 | Fuller et al. |
| 2017/0252064 A1 | 9/2017 | Staunton |
| 2017/0259042 A1 | 9/2017 | Nguyen et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Sethna |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0008407 A1 | 1/2018 | Maimon et al. |
| 2018/0042623 A1 | 2/2018 | Batiste |
| 2018/0193050 A1 | 7/2018 | Hawkins et al. |
| 2018/0193591 A1 | 7/2018 | Jaroch et al. |
| 2018/0235743 A1 | 8/2018 | Farago et al. |

(56) References Cited

U.S. PATENT DOCUMENTS

| | | |
|---|---|---|
| 2019/0021755 A1 | 1/2019 | Johnson et al. |
| 2019/0021759 A1 | 1/2019 | Krolik et al. |
| 2019/0029820 A1 | 1/2019 | Zhou et al. |
| 2019/0029825 A1 | 1/2019 | Fitterer et al. |
| 2019/0046219 A1 | 2/2019 | Marchand et al. |
| 2019/0192175 A1 | 6/2019 | Chida et al. |
| 2019/0209206 A1 | 7/2019 | Patel et al. |
| 2019/0216476 A1 | 7/2019 | Barry et al. |
| 2019/0239907 A1 | 8/2019 | Brady et al. |
| 2019/0255290 A1* | 8/2019 | Snyder ............. A61M 25/0053 |
| 2019/0269491 A1 | 9/2019 | Jalgaonkar et al. |
| 2019/0274810 A1 | 9/2019 | Phouasalit et al. |
| 2019/0298396 A1 | 10/2019 | Gamba et al. |
| 2019/0365411 A1 | 12/2019 | Avneri et al. |
| 2019/0366049 A1 | 12/2019 | Hannon et al. |
| 2020/0038628 A1 | 2/2020 | Chou et al. |
| 2020/0281611 A1 | 9/2020 | Kelly et al. |
| 2020/0353208 A1 | 11/2020 | Merhi et al. |
| 2021/0153883 A1 | 5/2021 | Casey et al. |
| 2021/0153884 A1 | 5/2021 | Casey et al. |
| 2021/0154433 A1 | 5/2021 | Casey et al. |
| 2021/0219821 A1* | 7/2021 | Appling ............... A61B 1/0055 |
| 2022/0117614 A1 | 4/2022 | Salmon et al. |
| 2022/0125450 A1 | 4/2022 | Sirhan et al. |
| 2023/0054898 A1 | 3/2023 | Gurovich et al. |

FOREIGN PATENT DOCUMENTS

| | | |
|---|---|---|
| CN | 103071195 A | 5/2013 |
| CN | 104507380 A | 4/2015 |
| CN | 104905873 A | 9/2015 |
| CN | 105007973 A | 10/2015 |
| CN | 105307582 A | 2/2016 |
| CN | 105726163 A | 7/2016 |
| CN | 106232059 A | 12/2016 |
| CN | 113040865 A | 6/2021 |
| DE | 20 2009 001 951 U1 | 4/2010 |
| DE | 10 2009 056 450 A1 | 6/2011 |
| DE | 10 2010 010 849 A1 | 9/2011 |
| DE | 10 2010 014 778 A1 | 10/2011 |
| DE | 10 2010 024 085 A1 | 12/2011 |
| DE | 10 2011 014 586 B3 | 9/2012 |
| DE | 20 2020 107013 U1 | 1/2021 |
| EP | 2301450 A1 | 3/2011 |
| EP | 2628455 A1 | 8/2013 |
| EP | 3302312 A1 | 4/2018 |
| EP | 3335647 A2 | 6/2018 |
| EP | 3 420 978 A1 | 1/2019 |
| EP | 4049704 A2 | 8/2022 |
| GB | 2498349 A | 7/2013 |
| JP | 9-19438 A | 1/1997 |
| WO | WO 93/04722 A2 | 3/1993 |
| WO | 94/24926 A1 | 11/1994 |
| WO | 97/27808 A1 | 8/1997 |
| WO | 97/38631 A1 | 10/1997 |
| WO | 99/20335 A1 | 4/1999 |
| WO | 99/56801 A2 | 11/1999 |
| WO | 99/60933 A1 | 12/1999 |
| WO | 01/21077 A1 | 3/2001 |
| WO | 02/02162 A2 | 1/2002 |
| WO | 02/11627 A2 | 2/2002 |
| WO | 02/43616 A2 | 6/2002 |
| WO | 02/070061 A1 | 9/2002 |
| WO | 02/094111 A2 | 11/2002 |
| WO | 03/002006 A1 | 1/2003 |
| WO | 03/018085 A2 | 3/2003 |
| WO | 03/030751 A1 | 4/2003 |
| WO | 03/051448 A2 | 6/2003 |
| WO | 2004/028571 A1 | 4/2004 |
| WO | 2004/056275 A1 | 7/2004 |
| WO | 2005/000130 A1 | 1/2005 |
| WO | 2005/027779 A2 | 3/2005 |
| WO | WO 2005/027751 A1 | 3/2005 |
| WO | 2006/021407 A2 | 3/2006 |
| WO | 2006/031410 A2 | 3/2006 |
| WO | 2006/107641 A2 | 10/2006 |
| WO | 2006/135823 A2 | 12/2006 |
| WO | 2007/054307 A2 | 5/2007 |
| WO | 2007/068424 A2 | 6/2007 |
| WO | 2008/034615 A2 | 3/2008 |
| WO | 2008/051431 A1 | 5/2008 |
| WO | 2008/131116 A1 | 10/2008 |
| WO | WO 2009/019664 A1 | 2/2009 |
| WO | 2009/031338 A1 | 3/2009 |
| WO | 2009/076482 A1 | 6/2009 |
| WO | 2009/086482 A2 | 7/2009 |
| WO | 2009/105710 A1 | 8/2009 |
| WO | WO 2009/103125 A1 | 8/2009 |
| WO | 2010/010545 A1 | 1/2010 |
| WO | 2010/046897 A1 | 4/2010 |
| WO | 2010/075565 A1 | 7/2010 |
| WO | 2010/102307 A1 | 9/2010 |
| WO | 2010/146581 A1 | 12/2010 |
| WO | 2011/013556 A1 | 2/2011 |
| WO | 2011/066961 A1 | 6/2011 |
| WO | 2011/082319 A1 | 7/2011 |
| WO | 2011/095352 A1 | 8/2011 |
| WO | 2011/106426 A1 | 9/2011 |
| WO | 2011/110316 A1 | 9/2011 |
| WO | 2012/052982 A1 | 4/2012 |
| WO | 2012/064726 A1 | 5/2012 |
| WO | 2012/081020 A1 | 6/2012 |
| WO | 2012/110619 A1 | 8/2012 |
| WO | 2012/120490 A2 | 9/2012 |
| WO | 2012/156924 A1 | 11/2012 |
| WO | 2013/016435 A1 | 1/2013 |
| WO | 2013/072777 A2 | 5/2013 |
| WO | 2013/105099 A2 | 7/2013 |
| WO | 2013/109756 A2 | 7/2013 |
| WO | 2014/081892 A1 | 5/2014 |
| WO | 2014/139845 A1 | 9/2014 |
| WO | 2014/169266 A1 | 10/2014 |
| WO | 2014/178198 A1 | 11/2014 |
| WO | WO 2014/188300 A1 | 11/2014 |
| WO | 2015/061365 A1 | 4/2015 |
| WO | 2015/134625 A1 | 9/2015 |
| WO | 2015/179324 A2 | 11/2015 |
| WO | WO 2015/179377 A1 | 11/2015 |
| WO | 2015/189354 A1 | 12/2015 |
| WO | 2016/010995 A1 | 1/2016 |
| WO | WO 2017/004234 A1 | 1/2017 |
| WO | WO 2017/097616 A1 | 6/2017 |
| WO | 2018/193603 A1 | 10/2018 |
| WO | WO 2018/178979 A1 | 10/2018 |
| WO | WO 2019/064306 A1 | 4/2019 |
| WO | WO 2019/079296 A1 | 4/2019 |
| WO | WO 2020/139979 A1 | 7/2020 |
| WO | WO 2021/016213 A1 | 1/2021 |
| WO | WO 2021/167653 A1 | 8/2021 |
| WO | WO 2022/020366 A2 | 1/2022 |

OTHER PUBLICATIONS

Extended European Search Report dated Aug. 5, 2021 issued in European Patent Application No. 21 16 7037.

Struffert, T., et al. "Intravenous flat detector CT angiography for non-invasive visualisation of intracranial flow diverter: technical feasibility" Eur Radiol 21:1797-1801 (2011).

* cited by examiner

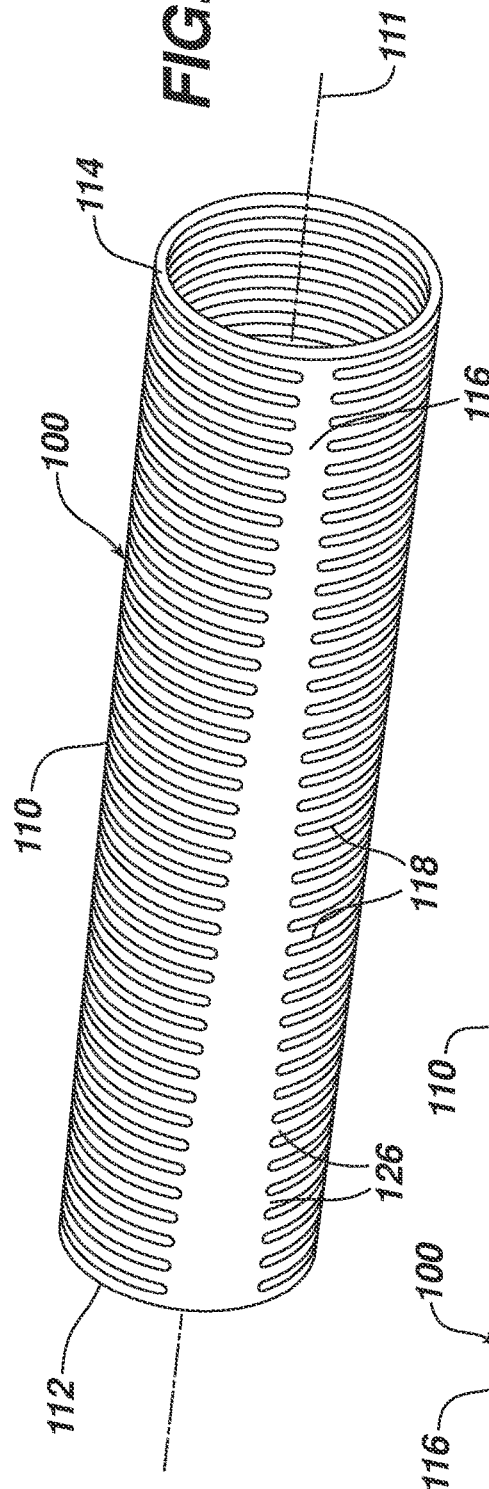
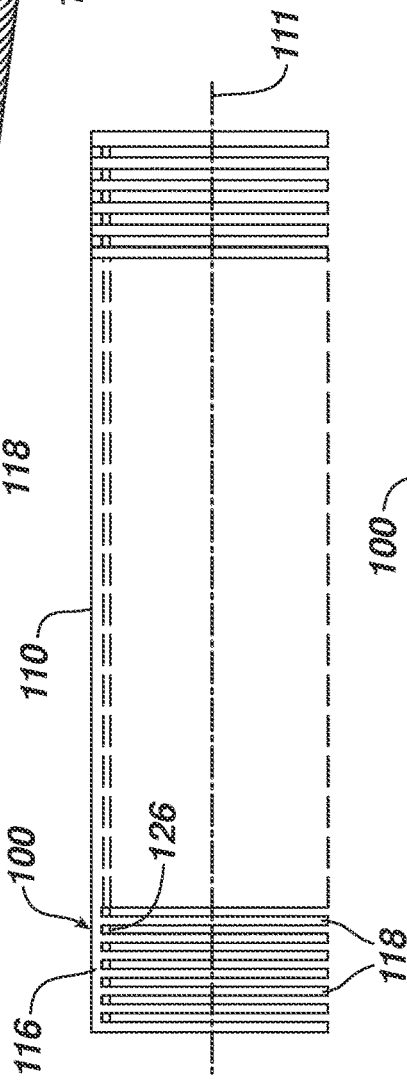
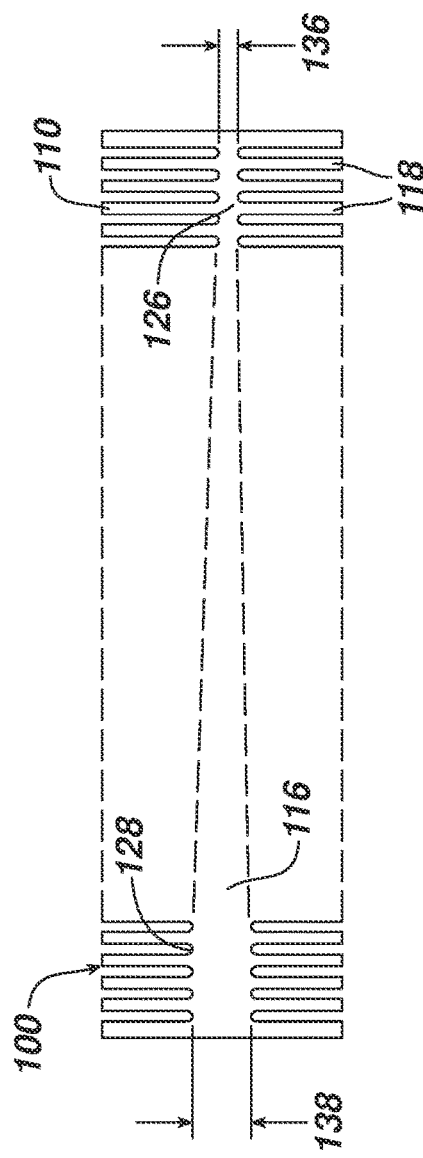

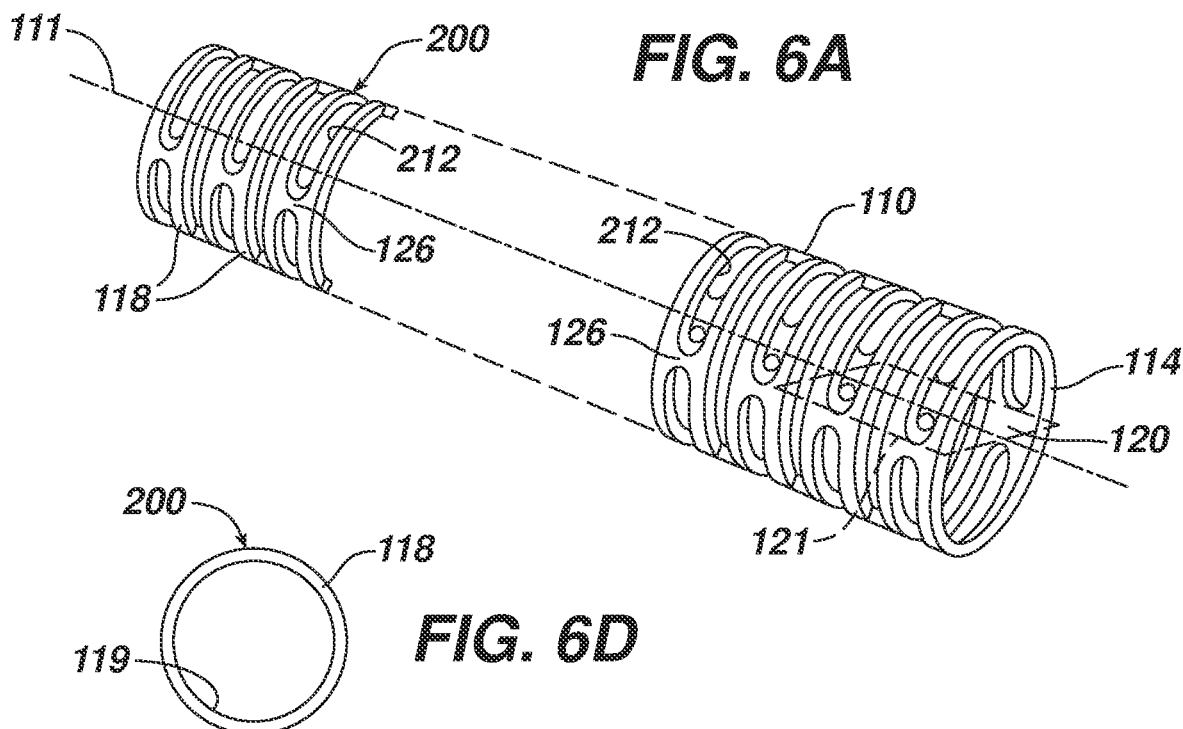
FIG. 6A
FIG. 6D
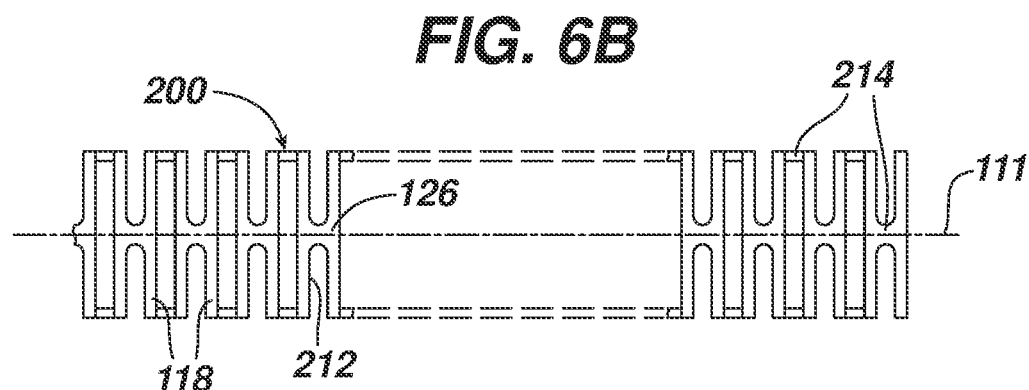
FIG. 6B
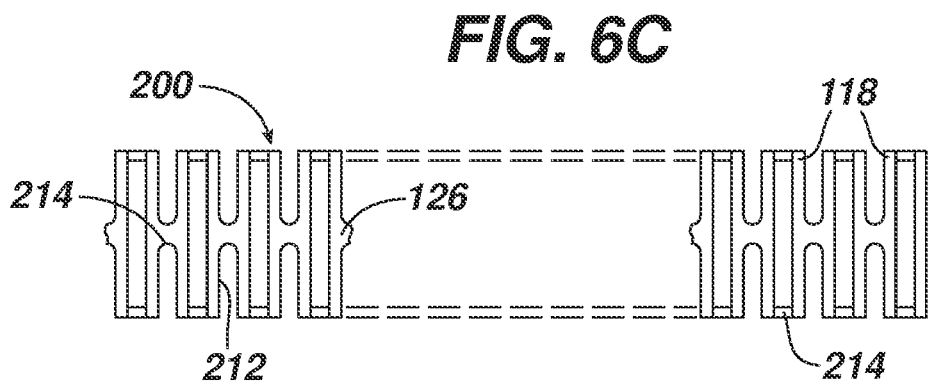
FIG. 6C

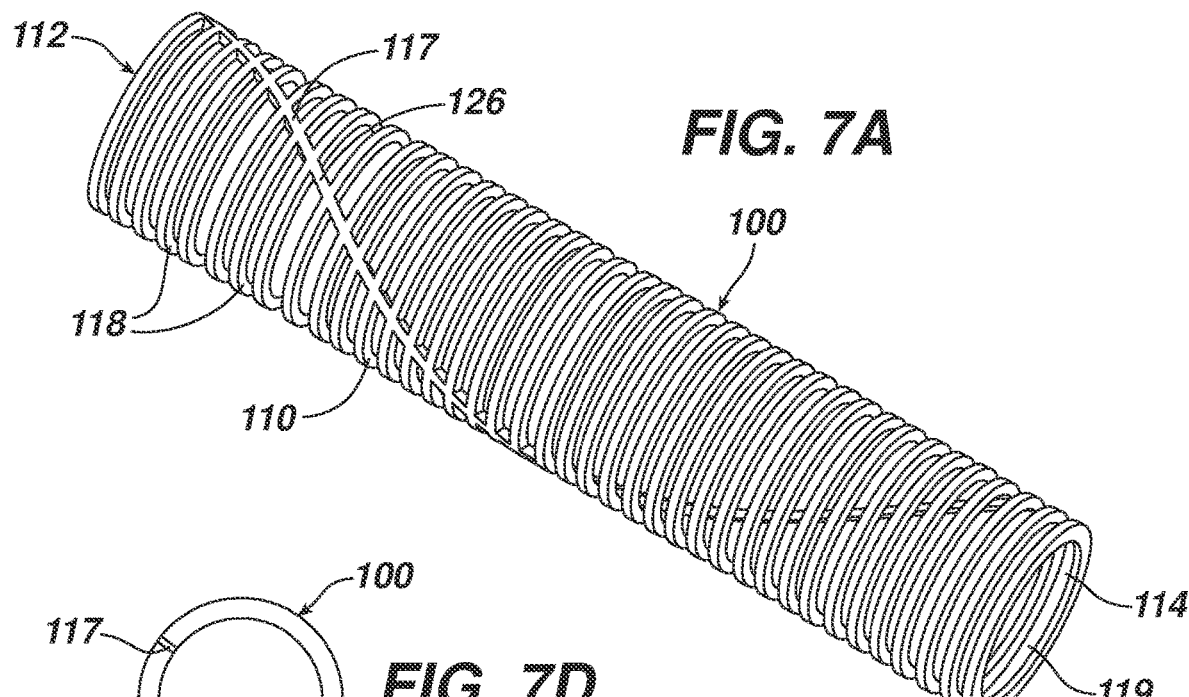
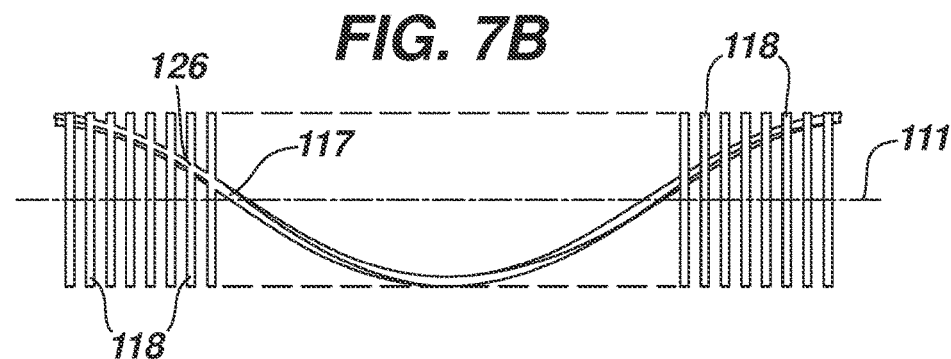
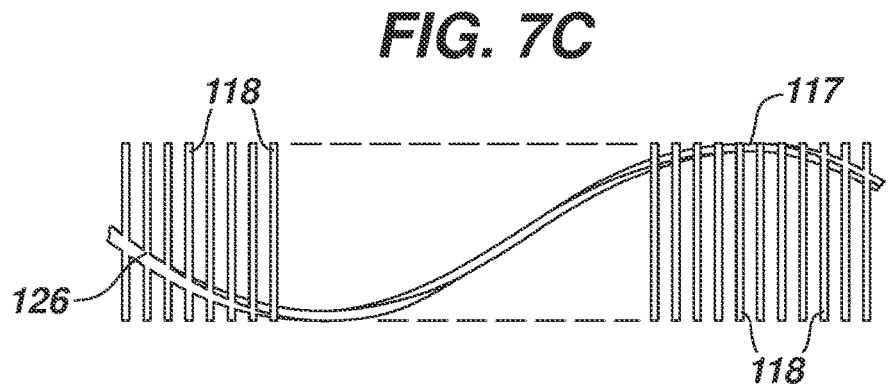

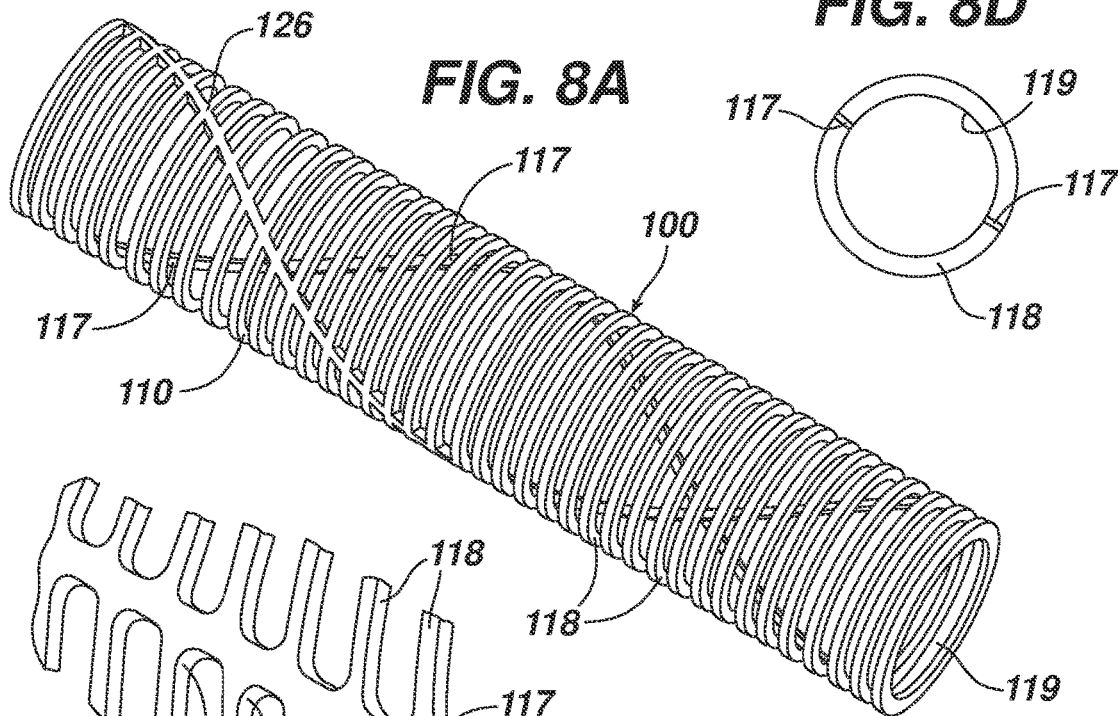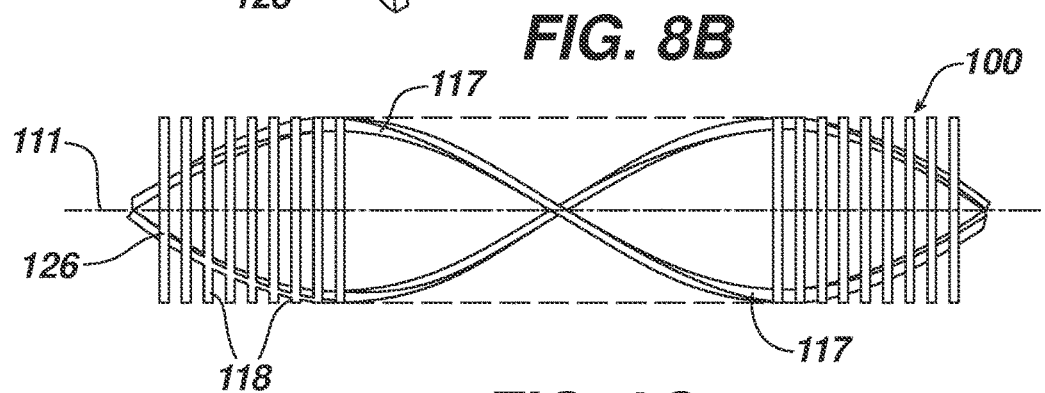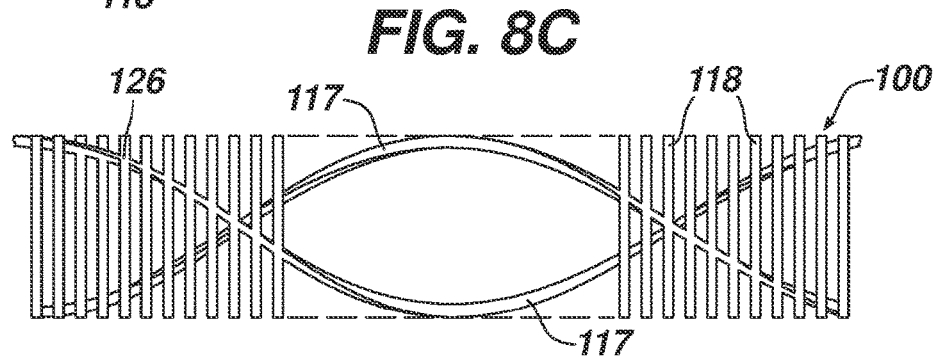

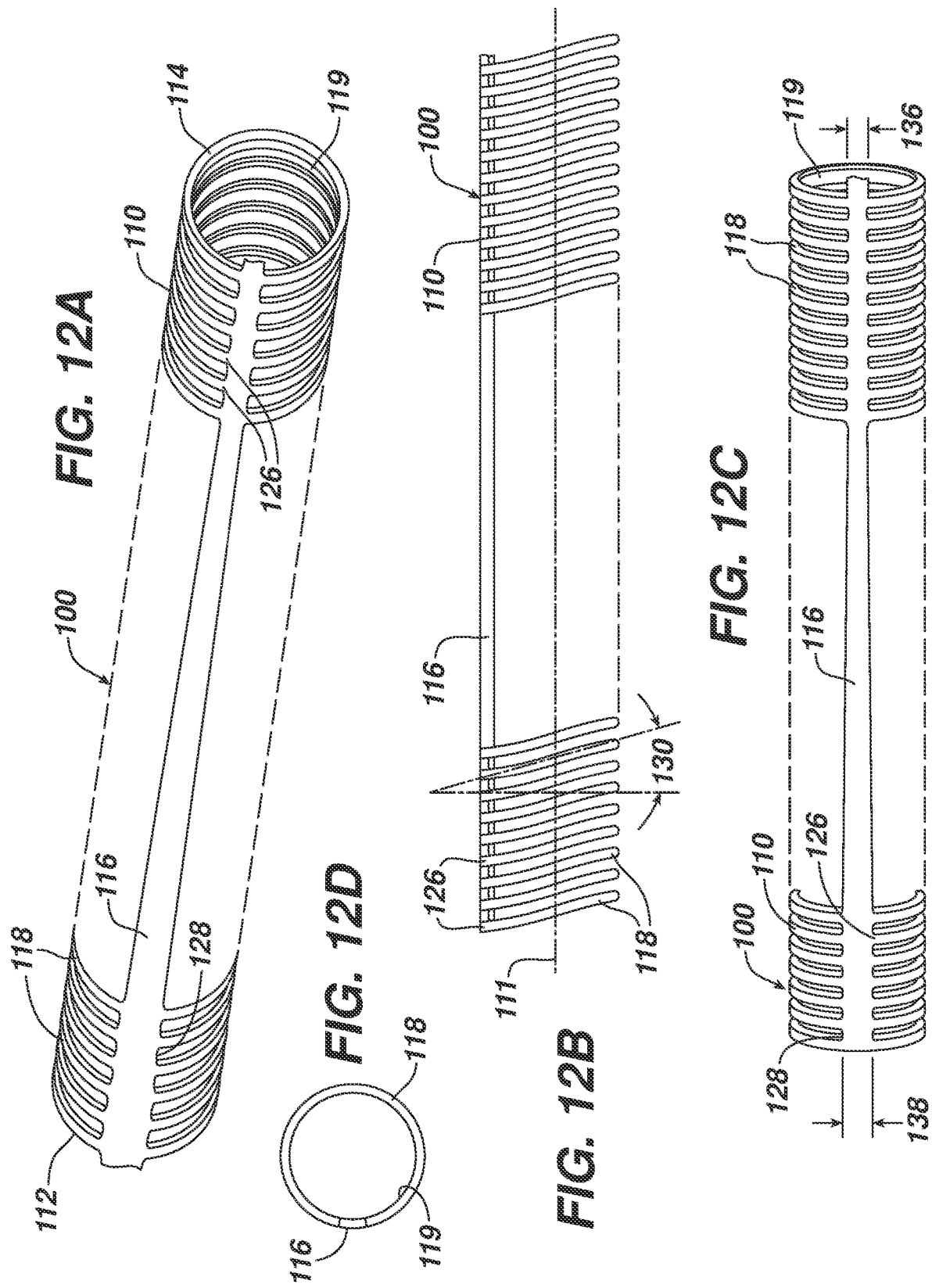

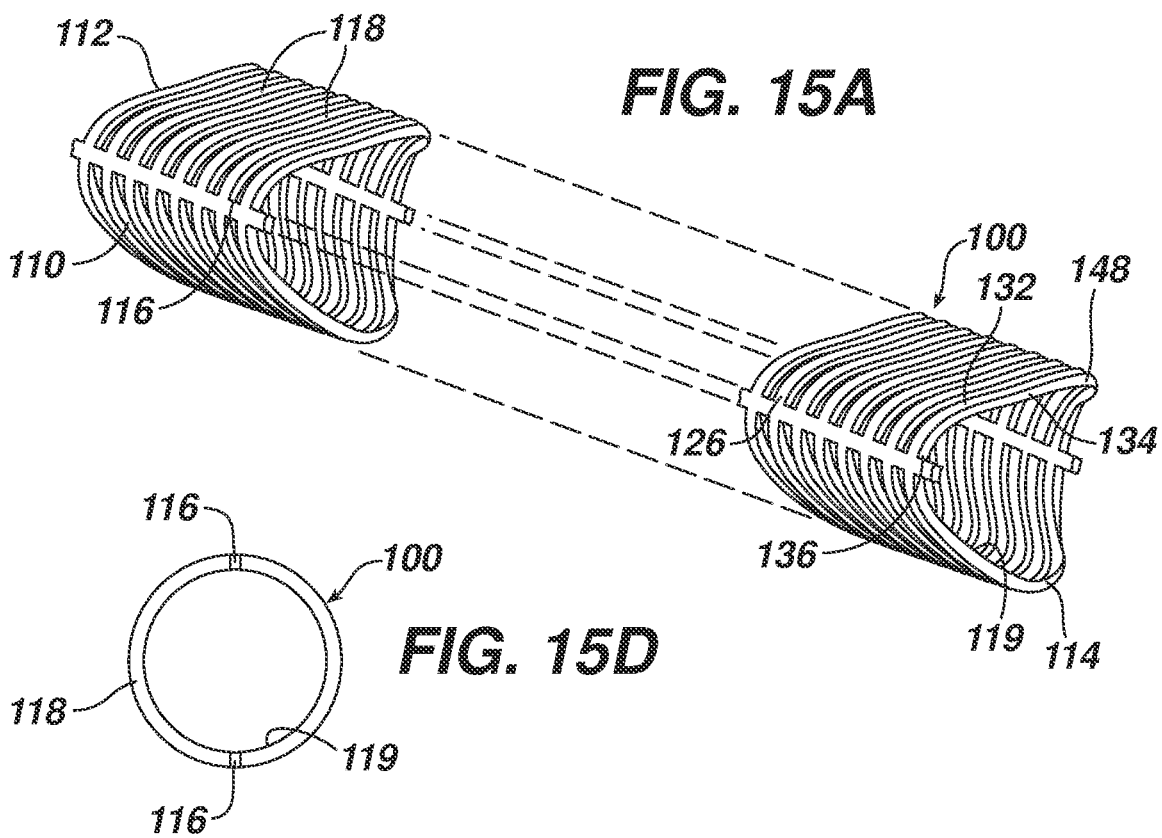
FIG. 15A
FIG. 15D
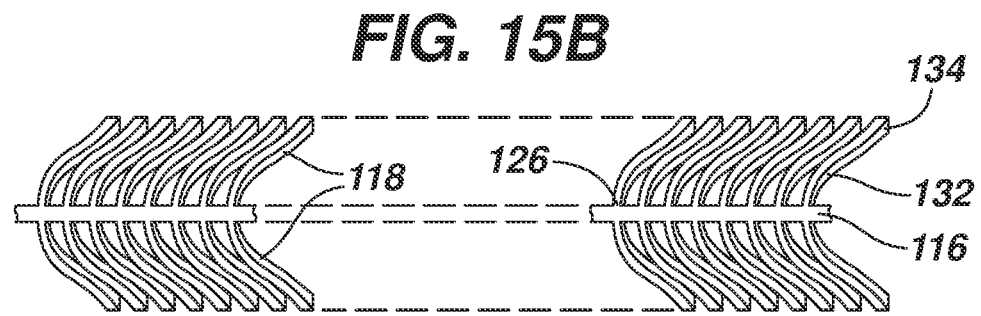
FIG. 15B
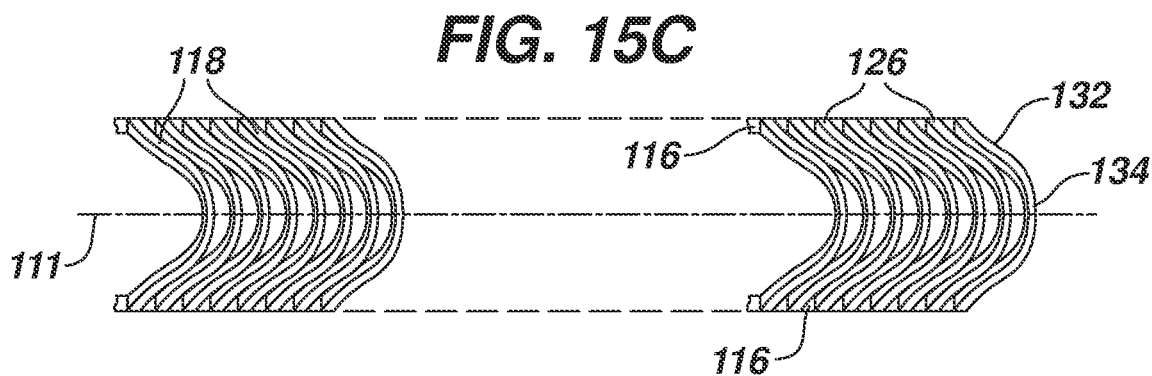
FIG. 15C

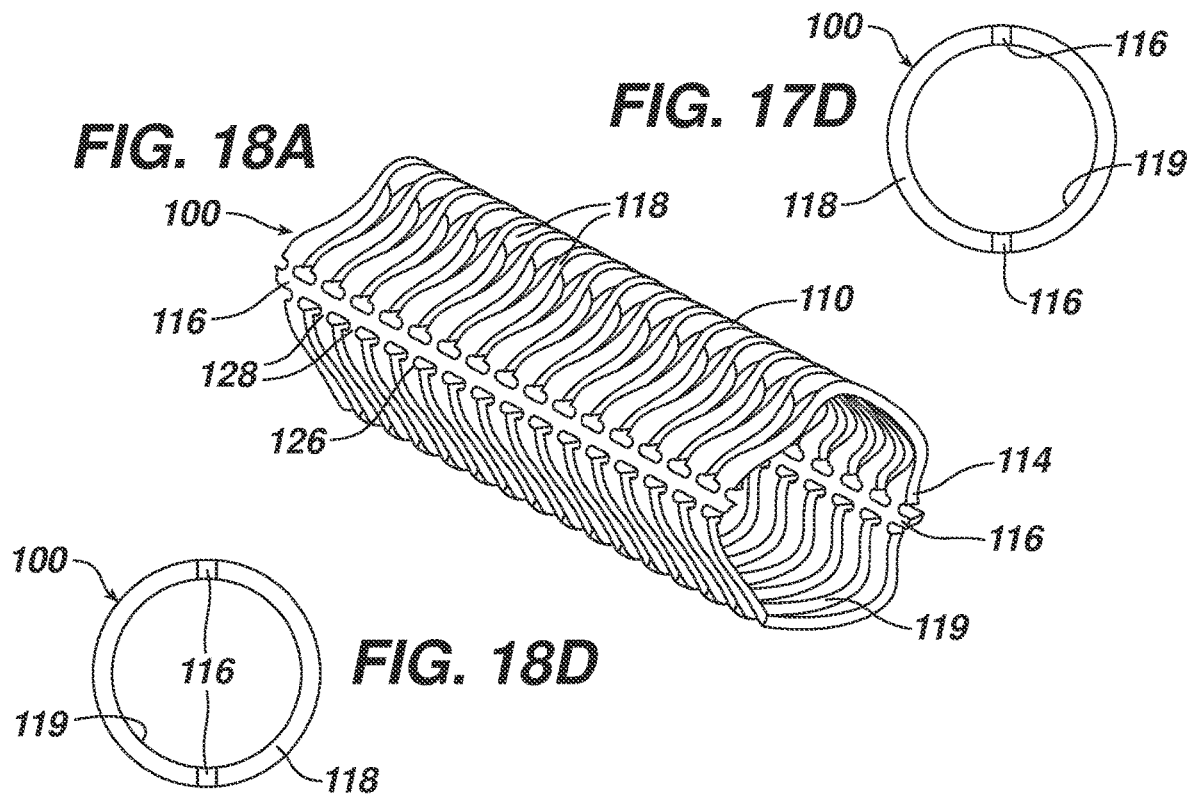
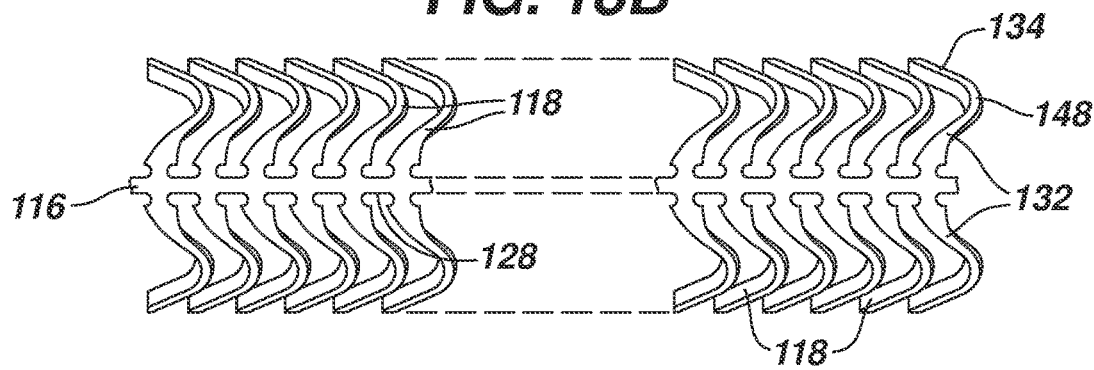
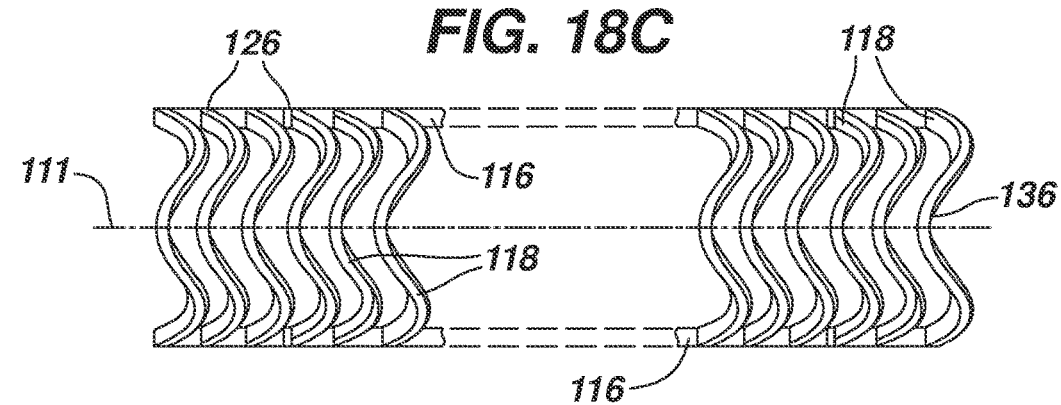

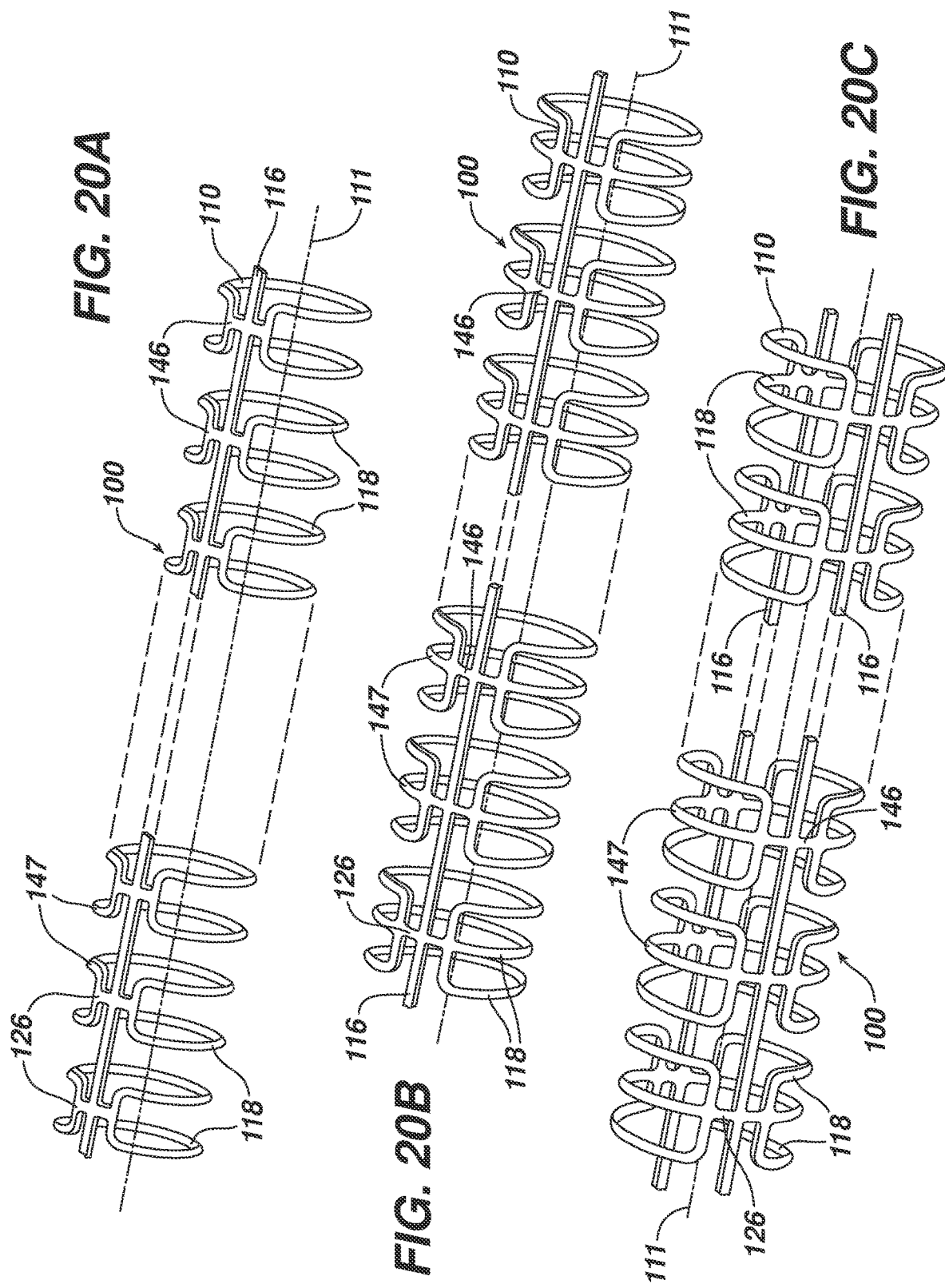

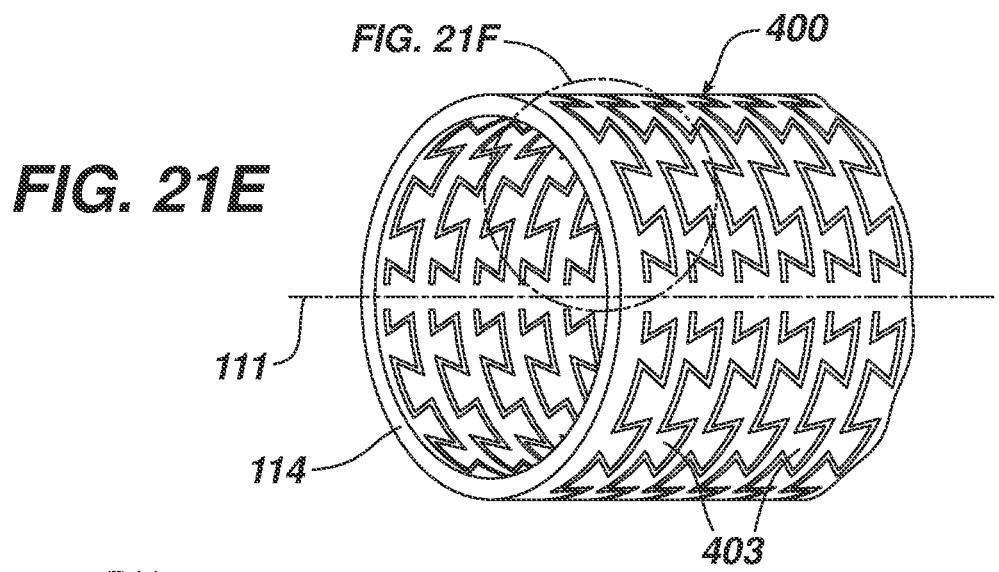
FIG. 21E
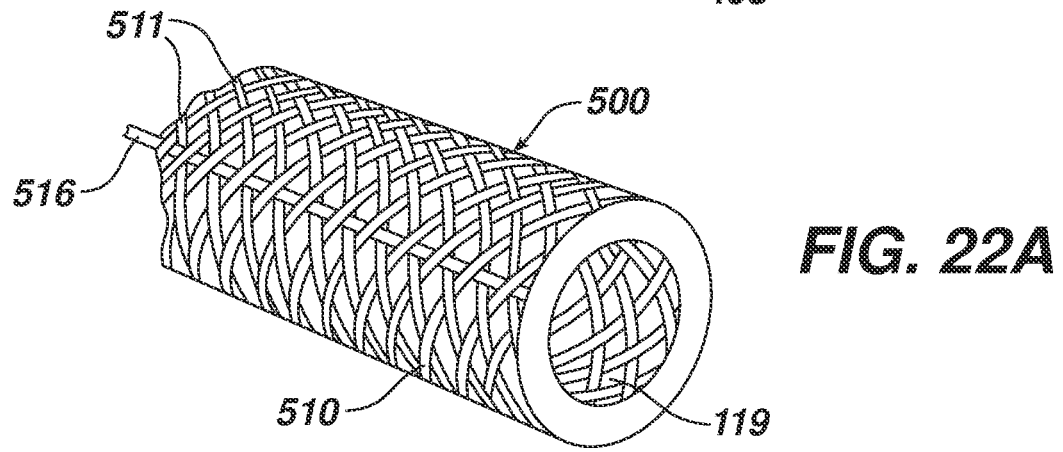
FIG. 22A
FIG. 22B
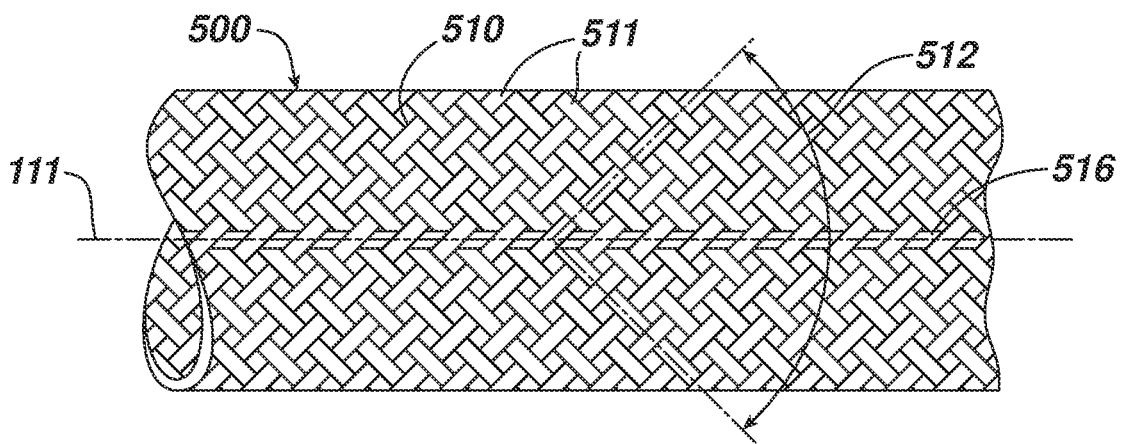

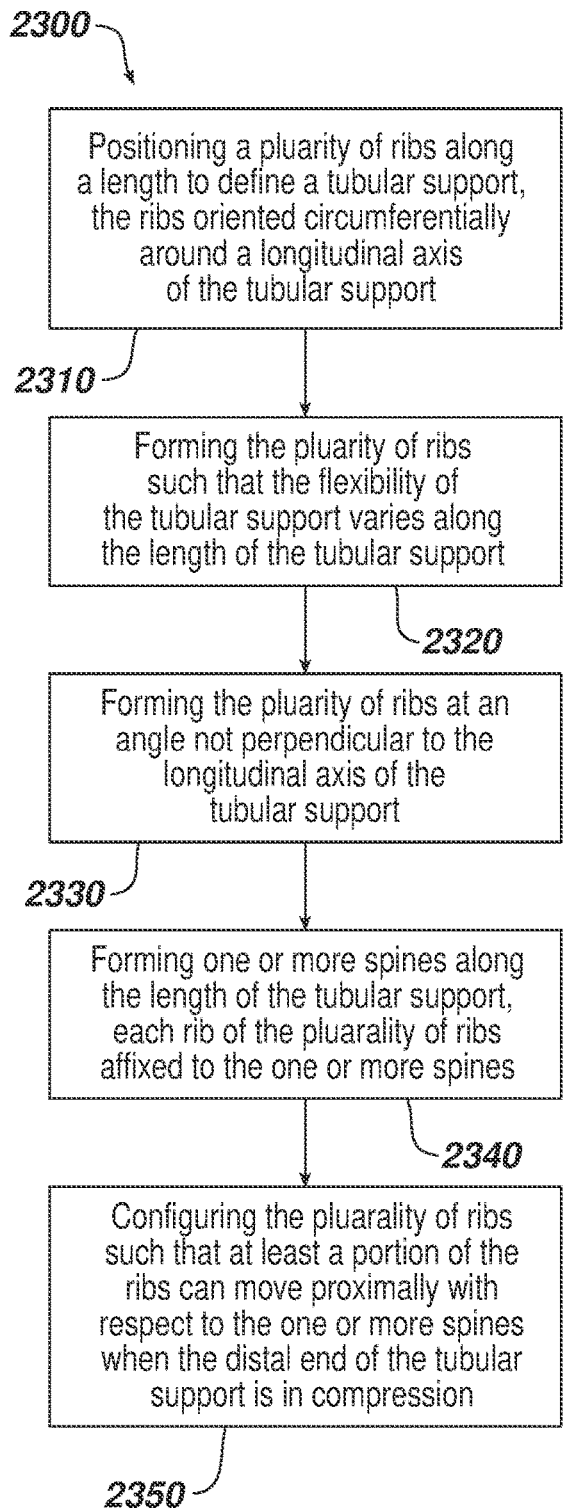
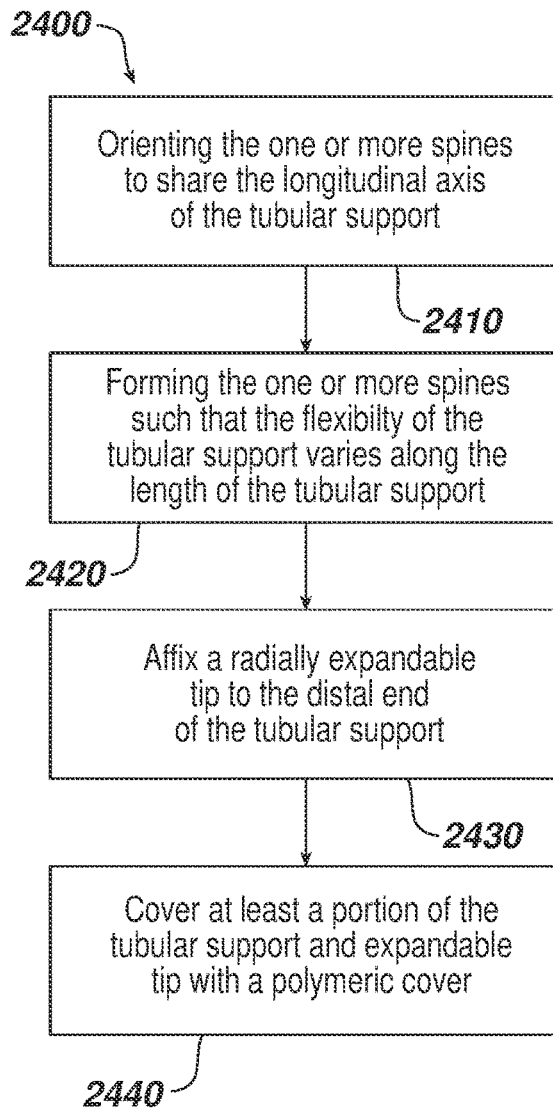

CATHETER TUBULAR SUPPORT

FIELD OF THE INVENTION

The present disclosure generally relates to devices and methods for removing acute blockages from blood vessels during intravascular medical treatments. More specifically, the present disclosure relates to a retrieval aspiration catheter.

BACKGROUND

Aspiration and clot retrieval catheters and devices are used in mechanical thrombectomy for endovascular intervention, often in cases where patients are suffering from conditions such as acute ischemic stroke (AIS), myocardial infarction (MI), and pulmonary embolism (PE). Accessing the neurovascular bed in particular is challenging with conventional technology, as the target vessels are small in diameter, remote relative to the site of insertion, and are highly tortuous.

In delivering effective devices to the small and highly branched cerebral artery system, conventional catheters must try and balance a number of factors. The catheter must be sufficiently flexible to navigate the vasculature and endure high flexure strains, while also having the axial stiffness to offer smooth and consistent advancement along the route. Newer designs have been introduced which utilize various methods to alter the stiffness between the proximal and distal portions of the catheter. But abrupt stiffness or geometric changes can hinder trackability, introduce significant stress concentrations, and potentially increase the likelihood of device kinking or buckling.

When aspirating with traditional catheters, such as a fixed-mouth catheter or a catheter which does not seal with an outer catheter, a significant portion of the aspiration flow ends up coming from vessel fluid proximal to the tip of the catheter, where there is no clot. This significantly reduces aspiration efficiency, lowering the success rate of clot removal. Furthermore firm, fibrin-rich clots can often be difficult to extract as they can become lodged in the tip of traditional fixed-mouth catheters. This lodging can cause softer portions to shear away from the firmer regions of the clot.

Other designs for aspirating catheters feature a large distal facing mouth to achieve maximum efficiency. For example, the mouth can be designed with a diameter that is considerably larger than the typical delivery catheter or sheath. As a result, the mouth is required to have both a flexible low-profile for delivery within an outer catheter but must deploy and expand to an enlarged configuration at the target site. The supporting tube of the catheter must be sufficiently flexible itself for access while having features capable of transmitting thrust loads effectively to the mouth at the distal tip.

However, many highly flexible body designs have a reduced diameter incapable of generating the required suction force, while designs with expandable members or separate suction extensions can lack the flexibility to navigate the neurovascular intact. Catheter elements must survive the severe mechanical strains imparted but also generate a sufficient radial force when expanded to prevent collapse of the catheter and the vessel under the suction of aspiration.

The present designs are aimed at providing an improved retrieval catheter with an expansile tip which incorporates these features to address the above-stated deficiencies.

SUMMARY

The designs herein can be for a clot retrieval catheter which can have a body support tube section which can be tailored to have sufficient flexibly so as to be capable of navigating highly tortuous areas of the anatomy, such as the neurovascular, to reach occlusive clots. The support tube can also be formed with or attached to an expandable catheter tip capable of providing local flow restriction/arrest within the target vessel with a large, clot-facing mouth. The catheter can also be compatible with relatively low-profile access sheaths and catheters for further deliverability advantages.

The clot retrieval catheter can have a substantially tubular body with a support framework defining a longitudinal axis. A large catheter lumen can be configured for the passage of guidewires, microcatheters, stent retrievers, and other such devices. The lumen can also direct aspiration to the catheter tip. The tubular body can extend from a proximal end and terminate at a distal end, at which an expandable tip can be integrally formed or fixedly connected. The tip can be configured to expand from a collapsed delivery configuration to an expanded deployed configuration when deployed at the site of an occlusive thrombus.

The support framework can have one or more axial spines extending longitudinally from the proximal end to the distal end. A series of loop ribs can be disposed along at least a length of the longitudinal spine or spines. The ribs of the support framework can define the internal lumen of the catheter extending therethrough. Each rib can intersect with the one or more spines at junction points. The junction points can have strain relief cutout features or similar geometry to relieve stress at the rib-spine junctions when the catheter is tracked through tortuous vessels in the vasculature. In some cases, rather than having independent junction points, multiple ribs may unite into a spine connector to improve the flexibility of the support tube by minimizing connections to the spine. Ribs can have wing segments with curves or taper so they merge into a spine connector which has a single junction point with each rib.

The ribs and spines can be monolithically formed though laser machining of a hypotube or extrusion of a polymeric tube. In another example the tubular body can be of metallic braid or coiled wire construction. The spine can be fixedly connected to, or formed integrally with, a part of the expansile tip.

At least a portion of the tubular section can form a seal or flow restriction with an outer catheter such that aspiration is directed to the distal tip of the clot retrieval catheter. A polymeric cover or membrane can be disposed around at least part of support framework and tip to enclose the catheter body. In another example, the cover can be a series of polymeric jackets having variable stiffness and flexure properties. The cover can be reflowed, adhered, and/or stitched to the framework of the support structure. The cover can further be coated with a low-friction layer or film to improve trackability and mitigate the risk of binding or excessive friction when delivered through an outer catheter.

The trackability and flexibility of the catheter in the vasculature can be tailored by adjusting properties of the support tube. For example, bending planes for the support tube can be defined through the location of the axial spines where the spine or spines are straight, parallel members. In another example, the spine or spines can be disposed in a spiral or helical pattern around the longitudinal axis of the support tube. The spine or spines can have a width in more proximal sections of the support tube that is different from the spine width in more distal sections. A transition from a one spine width to another can be a continuous taper or can transition between successively more flexible axial segments of the framework.

The struts forming the ribs of the framework of the support tube can have various widths, such that a first rib width of one rib is different than a second rib width of another rib. The ribs can also be a helical pattern, where the coiled structure can stagger the junction points between the ribs and the spines. The spacing, or pitch, of adjacent ribs can also be varied between the proximal end and the distal end of the support framework, such that one segment of the framework can have a dense rib pattern with greater stiffness than another segment with larger rib spacing.

In another example, the ribs can be cut or formed so they are disposed at an angle not perpendicular to the longitudinal axis of the support framework, such that the diameter of the internal lumen can change as the ribs move in response to tensile or compressive forces on the support tube during a thrombectomy procedure. The ribs can also be formed so they have a non-planar cross section and the profile of the rib struts has one or more proximal and/or distal curves or undulations. The ribs can also be configured to move relative to their respective junction points with the spine or spines so the support tube can locally expand for the passage of a captured clot that is firm or incompressible.

In another example, a support tube for forming the body of a catheter assembly can have a tubular support framework having a proximal end, a distal end, an internal lumen, and a pattern of radial slots configured around a longitudinal axis. The radial slots can be, for example, cut into the circumference of an extruded polymeric tube through various clocking positions so that they are discontinuous and not completely circumferential. The cuts can form slots that are a constant length of variable length. By aligning segments of the cuts, the slots in the support tube can define interrupted, continues, or both interrupted and continuous spines running the length of the tube.

In one instance, adjacent interrupted radial slots offset from each other by 90 degrees can form two interrupted spines. When offset in this fashion, the two interrupted spines can define two bending planes normal to each other and perpendicularly aligned through the longitudinal axis of the support framework. Additional spines and bending planes can be formed interrupting the cuts in additional places around the circumference of the tube and axially aligning or offsetting adjacent cuts as desired.

In another case, the radial slots can be cut in a helix pattern where the cuts of adjacent revolution twists are aligned to form one or more continuous and/or discontinuous spines. In one example, the helix pattern of interrupted slots can include at least two cuts per rotation. In another example, the helix pattern can include more than two cuts per rotation to form both continuous and discontinuous spines circumferentially offset from one another. Multiple cuts per rotation can allow flexibility along multiple different planes.

The radial slots of the support tube can be almost or completely circumferential around the longitudinal axis. With this configuration the slots divide the axial length of the support tube into a series of rings between the proximal end and the distal end of the tube. The rings can be a constant length or can vary in length. Individual rings can be joined to adjacent rings through a series of interlocking features around the circumference of each ring. Distal interlocking features can engage a particular ring with the next distal ring, while proximal interlocking features can engage with the next proximal ring. Overall flexibility of the tube can be varied by altering the number of interlocking features or changing their shape or circumferential spacing. Interlocking features can allow the support tube to transmit axial and torsional loads and minimize expansion of the tube in tension without the use of spines. Alternatively, one or more spines can be formed in the support tube by having the slots interrupted at points around the circumference and then aligning or offsetting the interruptions to create continuous or discontinuous spines.

In another example, a support tube for the body of a catheter can have a substantially cylindrical braided pattern formed by a plurality of strands about a longitudinal axis. The cylindrical braid of strands can define the lumen of the support tube. One or more spines can extend longitudinally along the braided pattern between its proximal end and distal end; and a polymeric cover can be disposed around at least a portion the braided pattern. The polymeric cover can encapsulate at least a portion of the braided pattern so as to fill in the gaps in the braid.

At least one of the one or more spines can interweave with the strands of the braided pattern. A design with spines woven into the braid can inhibit the structure from elongating in tension or shortening in compression. The spines can have variable width between the proximal end and the distal end of the braided pattern for improved bending flexibility.

In a braided pattern, an angle is formed where two strands come together in the weave. The angle formed by the strands can be used to tailor mechanical properties, and different angles can be used for different axial segments of the support tube. In one case, the angle of the braid pattern is in the range of approximately 20-90 degrees.

Also provided is a method for constructing a clot retrieval catheter. The method can have the step of positioning a plurality of ribs along a length to define a tubular support for the catheter. The ribs can be circular or of some other shape and be oriented around a longitudinal axis of the tubular support. The ribs can also be oriented at an angle not perpendicular to the axis, allowing them to move under the forces of the thrombectomy procedure. When a clot is drawn into the distal mouth of the catheter, compressive forces can be transferred to the ribs to cause at least a portion of the ribs to move proximally relative to the longitudinal axis, effectively increasing the local diameter of the inner lumen of the catheter.

One or more axial spines can be formed along the length of the tubular support, connecting the plurality of ribs at junction points and allowing thrust to be transmitted though the tubular support. In one example, the spine or spines can be formed integrally with the ribs of the support, such as a laser cut hypotube. The spine or spines can be linear and parallel to the longitudinal axis or can be formed as a spiral or helix about the axis. A radially expandable tip can be connected to, or formed integrally with, the distal end of the tubular support. A further step can involve having a polymeric cover disposed around at least a part of the tubular support and expandable tip. The cover can be elastic so that it stretches as the tip expands, or it can be baggy or loose around the frame so that the whole radial force of the tip can be transmitted to the walls of a vessel.

Another step can involve forming and positioning the ribs and spines to tailor the bending stiffness of the catheter tubular support at different portions along the length. The ribs can, for example, be spaced more densely at the proximal end, or have a thicker strut width. Similarly, the spine or spines can have an increased width proximally and taper to a narrower profile distally, to provide good pushability and give increased distal flexibility for access.

Bending stiffness can be tailored either by or a combination of varying the cut width and rib width. Where the cut width is kept constant, for instance, the width of a laser beam, the rib width and/or spine(s) width can be varied to tailor bending stiffness. Where the cut width is varied, the rib width can be kept constant or varied and the laser can be used to remove pieces of material. It is appreciated that by using cut width equal to that of the laser beam, no pieces of material are removed, and the cost of manufacture is greatly reduced. On the other hand, by using the laser to remove pieces of material, greater variation in shaft design can be achieved. It is also appreciated that combination of both approaches may be used such that the shaft incorporates more cost-effective cutting/processing means at the proximal end and more costly approaches are kept to a specific distance at the distal end where more complicated cuts can be required to achieve the desired performance. For example, the distal end may include a length of 20 cm with cuts that remove pieces of material and also include the cutting of an expandable tip. In another example, a proximal section of the shaft may be cut from SS and be joined to a distal section cut from NiTi in order to reduce overall cost while affording the benefits of NiTi to the distal end of the device where it is required for enhance resilience to tight bending curves and also to provide expansion and recovery characteristics. For such a device, the SS and NiTi sections can be joined by welding directly, by welding to a more weldable intermediate metal such as platinum. As an alternative, laser cut interlocking features can hold both cut tubes together in a longitudinal direction. An outer membrane cover or jacket can hold the tubes together in a radial direction.

Other aspects and features of the present disclosure will become apparent to those of ordinary skill in the art, upon reviewing the following detailed description in conjunction with the accompanying figures.

BRIEF DESCRIPTION OF THE DRAWINGS

The above and further aspects of this invention are further discussed with reference to the following description in conjunction with the accompanying drawings. The drawings are not necessarily to scale, emphasis instead being placed upon illustrating the principles of the invention. The figures depict one or more implementations of the inventive devices, by way of example only, not by way of limitation.

FIG. 3a-d are a series of views of a support tube according to aspects of the present invention;

FIG. 6a-d are a series of views of another support tube according to aspects of the present invention;

FIG. 7a-d are a series of views of another support tube with a helical spine according to aspects of the present invention;

FIG. 8a-d are a series of views of another support tube with dual helical spines according to aspects of the present invention;

FIG. 8e is a representation of the strain relief cutouts in a support tube according to aspects of the present invention;

FIG. 12a-d are a series of views of another support tube according to aspects of the present invention;

FIG. 15a-d are a series of views of another support tube according to aspects of the present invention;

FIG. 17a-d are a series of views of another support tube according to aspects of the present invention;

FIG. 18a-d are a series of views of another support tube according to aspects of the present invention;

FIG. 20a shows a support tube with multiple ribs sharing spine connections according to aspects of the present invention;

FIG. 20b shows an alternate support tube with multiple ribs sharing spine connections according to aspects of the present invention;

FIG. 20c illustrates another support tube with multiple ribs sharing spine connections to multiple spines according to aspects of the present invention;

FIG. 21e illustrates another puzzle cut support tube with rings joined by interlocking features and twin spines according to aspects of the present invention;

FIG. 22a-b are views of a support tube of braided construction according to aspects of the present invention; and FIG. 23-24 are flow diagrams outlining a method of use for the system according to aspects of the present invention.

DETAILED DESCRIPTION

Figure 1:
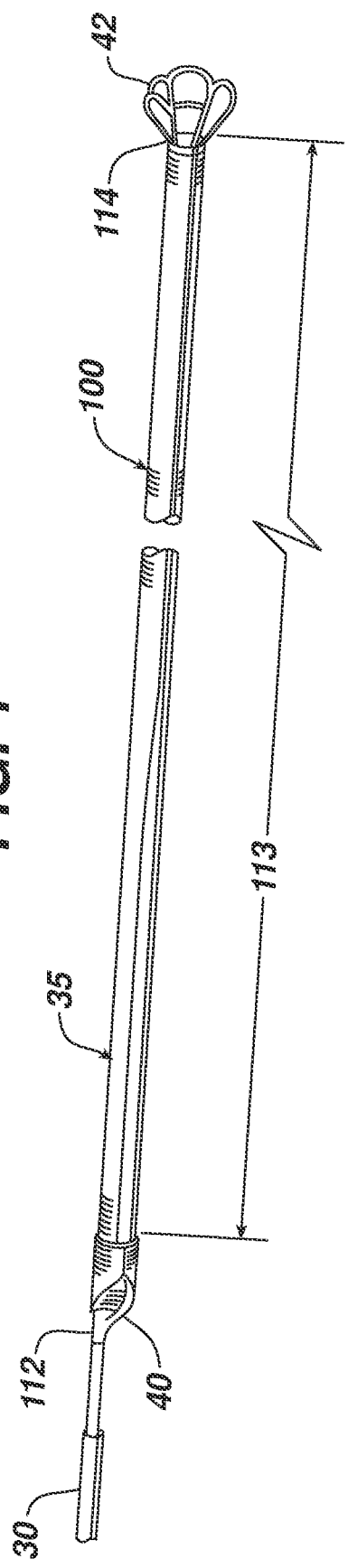
FIG. 1 is an isometric view of a clot retrieval catheter with a tubular support and an expandable distal tip according to aspects of the present invention.
Figure 3D:
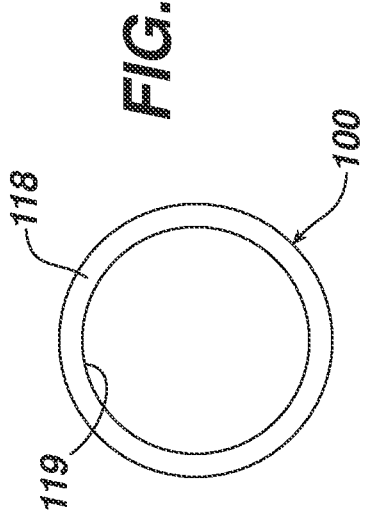

The objective of the disclosed designs is to create a clot retrieval catheter with a radially expandable distal tip for local flow restriction/arrest and a tailored, highly flexible body section capable of navigating the tortuous areas of the vasculature to reach an occlusive clot. Such advantages can be especially beneficial in the case of stroke intervention procedures, where vessels in the neurovascular bed are small and very tortuous, where a carefully designed axial and bending stiffness profile can inhibit kinking and binding. The catheter can also be compatible with relatively low-profile access sheaths and catheters, so that a puncture wound in the patient's groin (in the case of femoral access) can be easily and reliably closed. The support structure can also feature internal and/or external low-friction liners, and an outer polymer jacket or membrane disposed around the support structure.

An advantage of using an expanding mouth clot retrieval catheter with an outer catheter is that if both have the flexibility to reach a target, the clot retrieval catheter can be retracted with a clot through the outer catheter such that the outer catheter is left in place to maintain access at the treatment location. While it is appreciated that certain clots may also require that the outer catheter be retracted with the clot and inner clot retrieval catheter, the majority of clots are likely to be removed through the inner clot retrieval catheter. Further, there will be greater confidence that the lumen of the outer catheter is clean of debris for reduced risk during contrast injection that potential thrombus remnants may be dislodged from the catheter during contrast injection as is the case with using a standard intermediate catheter. To counteract this, a user can remove the intermediate catheter to flush any thrombus remnants outside of the body prior to injecting contrast, at the cost of losing access to the target treatment location. By comparison, the present design provides a further means to minimize the number of catheter advancements required to treat a patient, thereby reducing the likelihood of vessel damage and the associated risk of vessel dissection in cases where multiple passes are required.

While the description is in many cases in the context of mechanical thrombectomy treatments, the systems and methods may be adapted for other procedures and in other body passageways as well.

Specific examples of the present invention are now described in detail with reference to the Figures, where identical reference numbers indicate elements which are functionally similar or identical. Accessing the various vessels within the vascular, whether they are coronary, pulmonary, or cerebral, involves well-known procedural steps and the use of a number of conventional, commercially available accessory products. These products, such as angiographic materials, rotating hemostasis valves, and guidewires are widely used in laboratory and medical procedures. When these or similar products are employed in conjunction with the system and methods of this invention in the description below, their function and exact constitution are not described in detail.

Turning to the figures, in FIG. 1 there is illustrated a clot retrieval catheter 35 for use in retrieving a clot or obstruction from a vessel of a patient. The clot retrieval catheter 35 can have an elongate proximal catheter shaft 30 or guidewire for manipulating and delivering the catheter, a support tube 100 forming the main catheter body extending between a proximal end 112 and a distal end 114, and an expansile tip 42 at the distalmost end of the retrieval catheter. The expansile tip 42 can be sized and configured such that when deployed at the target site, it expands radially to atraumatically contact the inner vessel walls to provide flow restriction/arrest to prevent the unwanted aspiration of blood proximal to the tip and a large opening for aspirating and receiving the clot.

The flexibility of the catheter 35 can enable a physician to use a smaller diameter standard sheath or outer access catheter (not shown) to rapidly create a path and gain access to the vicinity of an occlusion. The aspiration catheter can be a rapid-exchange (RX) type similar to that illustrated in FIG. 1, wherein a proximal guidewire 30 is bonded with a proximal joint 40 of a support tube 100 defining the catheter body. The support tube can have a length 113 between a proximal end 112 and a distal end 114. Preferably, the expansile tip 42 is expanded at the treatment location to avoid having to advance an expanded tip through the vasculature, allowing the length 113 of the support tube to be relatively short. For clots located in the anterior or posterior cerebral arteries, the length 113 can be greater than 5 cm so that it can extend from the outer catheter right up to the proximal face of the clot, but less than 40 cm so that a minimal length can remain inside the distal end of the outer catheter while maximizing the afforded volume of the combined outer/retrieval catheter for aspiration. A shortened length 113 of the distal section also improves trackability and flexibility of the system to access targets.

The transition at the proximal joint 40 can include an ability to seal with an outer sheath or intermediate catheter, supplied with or separately from the clot retrieval catheter 35. A seal can allow an aspiration source connected to the proximal end of the intermediate catheter to have a direct connection to the mouth at the distal tip 42 of the clot retrieval catheter with little or no loss in negative pressure between the aspiration source and the mouth.

The guidewire 30 can be solid or can be a composite of multi-layer materials, such as a solid core and outer tubular portions (for example, a Nitinol core with an outer polymer jacket). The guidewire 30 can also be formed with features that interlock with features of the proximal joint 40 of the catheter body support tube 100 so that a mechanical lock is configured between the guidewire and support tube. Heat-shrink, reflowed polymer, and/or adhesives may be used to reinforce the connection between the guidewire and the support tube.

The expanded deployed form of the expansile tip framework 42 at the distal end 114 of the clot retrieval catheter 35 can take on a flared or funnel shape. By incorporating a funnel shape in to the expansile tip, a clot can be progressively compressed during retrieval to a smaller diameter so that it can be aspirated fully through the catheter an into an aspiration syringe or canister. Because of this compression, it is less likely for firm, fibrin rich clots to become lodged in the tubular section of the clot retrieval catheter. If the clot does become lodged in the mouth of the tip, the expanded mouth will protect the clot and prevent it from dislodging as the aspiration suction is maintained and the catheter 35 is retracted into the sheath or outer catheter.

The funnel design of the expansile tip of the disclosed examples can be an integral lattice laser cut directly and integrally with the support tube of the catheter shaft. Alternately, the expansile tip lattice can be injection molded as a single piece and attached to the support tube through heat welding, adhesives, or similar means. The expansile tip 42 of the clot retrieval catheter 35 can be designed to expand to a wide range of target vessel diameters, such as a carotid terminus (3.2-5.2 mm), a horizontal M1 segment of the Middle Cerebral Arteries (1.6-3.5 mm), and/or the Internal Carotid Artery (ICA, 2.7-7.5 mm). If the catheter is then retracted from an M1 segment to the ICA (or another route with a proximally increasing vessel inner diameter), the expansile tip 42 will continue to seal the vessel across a range of vessel sizes. Further, a tip capable of a range of target vessel diameters can also seal at vessel bifurcations which can have a wider cross-sectional area than the vessel proximal and vessels distal to the bifurcation. Preferably, the expansile tip 42 of the catheter 35 is expanded at the treatment location to avoid having to advance the expanded tip through the vasculature.

The distal section of the aspiration clot retrieval catheter 110 has good thrust and trackability characteristics to aid in advancing it to the target location. It can therefore have multiple designs, or be fabricated from multiple materials, to give a reducing stiffness profile along the length to minimize insertion and retraction forces. In one example, the support tube 100 can be laser cut from a hypotube and formed integrally with an expanding frame portion of the distal tip 42. In another example, the support tube can be an injection molded polymer or a metal braid or weave supporting structure. Features can also be incorporated which bias bending about certain planes or encourage twisting to reduce the imparted strains. In this way the catheter will maintain excellent lateral flexibility but will not tend to expand in or kink compression.

The catheter 35 can also have a cover or membrane disposed around or encapsulating the support tube 100 and expansile tip 42. In the disclosed examples illustrated in the figures herein the jacket or membrane is often not shown for clarity of the underlying support structure, and the construction and appearance of such a membrane can be appreciated by those of skill in the art. Suitable membrane materials can include elastic polyurethanes such as ChronoPrene®, which can have a shore hardness of 40 A or lower, or silicone elastomers. A single or variable stiffness cover can be extruded or post-formed over the support tube 100. The cover can also be laminated, or heat welded to the structure.

Alternatively, the cover can also be a formed from a series of polymer jackets. Different jackets or sets of jackets can be disposed discrete lengths along the axis of the support tube 100 in order to give distinct pushability and flexibility characteristics to different sections of the tubular portion of the catheter 35. By configuring the jackets in an axial series, it is possible to transition the overall stiffness of the catheter from being stiffer at the proximal end to extremely flexible at the distal end. Alternately, the polymer jackets of the cover can be in a radial series disposed about the support tube in order to tailor the material properties through the thickness. In a further example, transitions between jackets can be tapered or slotted to give a more seamless transition between flexibility profile of abutting jackets in longitudinal series.

In order to allow for smooth delivery of the clot retrieval catheter through an outer catheter, the outer surface of the membrane or outer jackets can be coated with a low-friction or lubricious material, such as PTFE or FEP. In another example, a low-friction inner liner can also be applied to the inner circumference of the support tube 100. Alternately, a lubricant (such as silicone oil or molybdenum disulfide) can also be used, or a coating such as a hydrophilic coating. In a further example, the inner or outer surfaces of the membrane, or the tubular section of the catheter body if formed from a polymeric extrusion, can be impregnated with a low-friction component that migrates to the surface such that the application of low-friction liners are not required.

Figure 2:
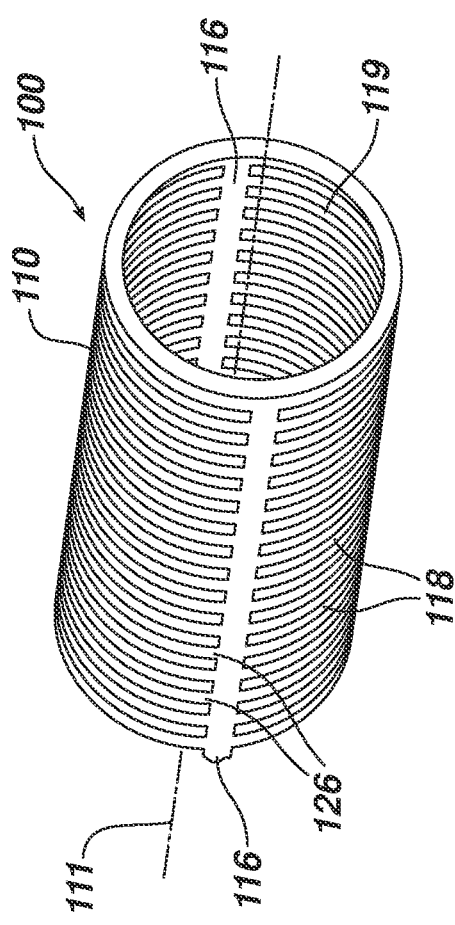
FIG. 2 shows an isometric view of a tubular support with circular ribs and two axial spines, according to aspects of the present invention.
Figures 4A, 4B, 4C, 4D:
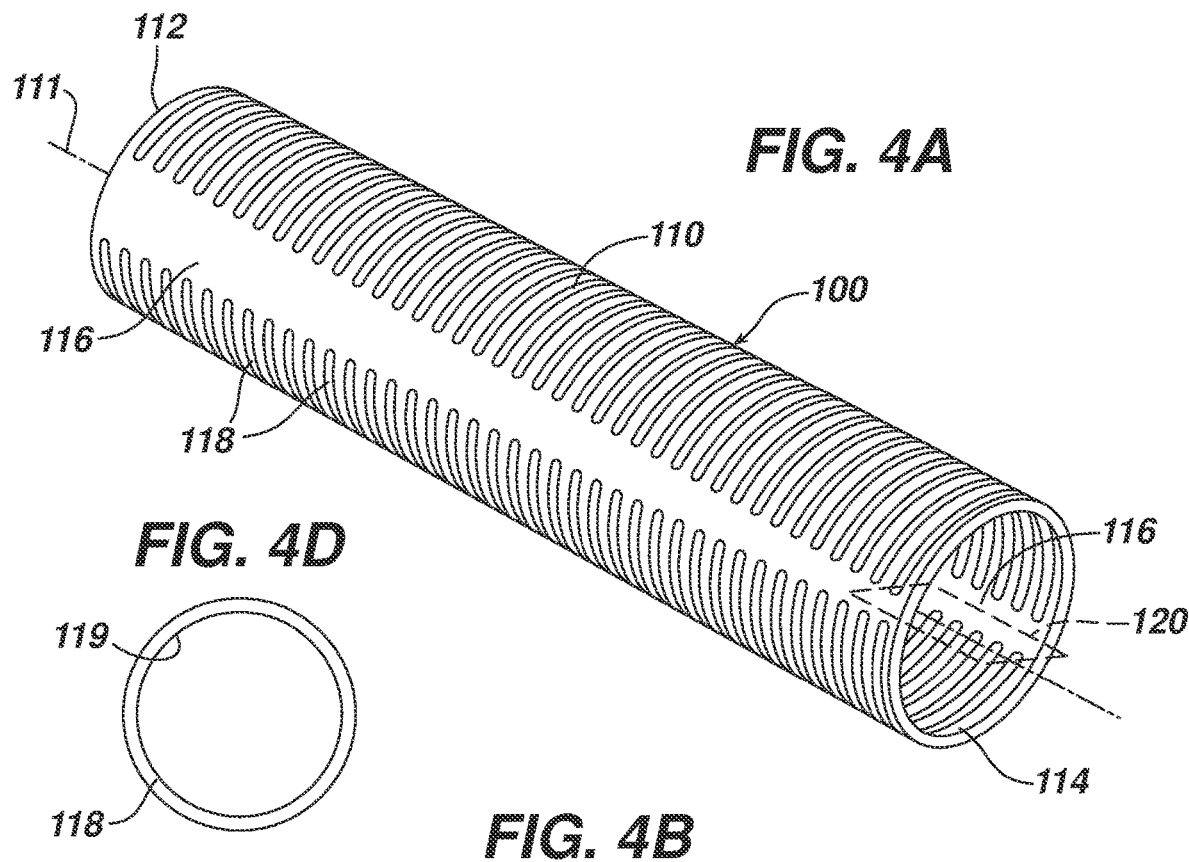
FIG. 4a-d are a series of views of another support tube according to aspects of the present invention.

The support tube 100 structure of framework 110 of the clot retrieval catheter 35 can be of many different configurations. In one example, the support tube 100 can have a structure similar to that illustrated in FIG. 2. The tube 100 can have a supporting framework 110 with one or more axial spines 116 extending distally from the proximal end 112 to the distal end 114 parallel to the longitudinal axis 111. The spine can be of tubular or wire construction such that it has good axial stiffness for advancing and retracting the catheter with sufficient lateral flexibility for navigating within the vascular. Use of multiple spines encourages flexing along defined planes and while reducing the possibility of the support tube 100 elongating under tensile loads, such as when the expansile tip is withdrawn into the mouth of the outer catheter. Running the length of the axial spine or spines can be a plurality of ribs 118 that can be axisymmetric with the longitudinal axis 111 of the clot retrieval catheter 35. The ribs 118 can define a central lumen 119. The ribs 118 can be a simple circular configuration as shown or take a more complex shape as required.

The ribs 118 and the one or more axial spines 116 of the tubular support framework 110 can be formed from laser-cutting tube stock such as a hypotube, or of otherwise similar construction including strands with braids, weaves and/or coils with overlaid or interwoven spines. This enables the support tube 100 to have good push and torque characteristics, kink resistance, resistance to collapse under aspiration, and solid resistance to tensile elongation. Commonly used materials include Nitinol and familiar medical-grade stainless-steel alloys like 304 and 316. Hypotubes of different materials, such as stainless-steel for the proximal section of the tubular support and Nitinol for a distal portion of the tubular support tube and for the expansile mouth, said different materials being joined by welding, bonding, or by holding interlocking features in place with the inner and/or outer polymer jacket materials.

In another example, one or more of the spines 116 can be formed integrally with the distal expandable tip 42. This configuration allows the spines 116 to continue distally of the tube as a continuous member, which can yield good pushability characteristics while maintaining a gentler bending stiffness transition between the support tube 100 and the tip 42.

Although illustrated as flush with the ribs 118, it can be appreciated that the spine or spines 116 can also be located mid-wall or tangent to the inner wall of the support framework 110.

Tailoring of the stiffness and changes in stiffness for the catheter is important for situations where the distances and tortuosity can be significant, such as when it must be advanced from a patient's inner thigh, over the cardiac arch, and up into the neurovascular blood vessels inside the skull. When forming the framework 110, the dimensioning of the cuts in a hypotube to form the ribs 118 and spines 116 can be used to tailor this stiffness. For example, the ribs can be cut to various widths and spacing density. The cuts can be circumferentially continuous and terminate on either side of an axial spine 116, or the cuts can be discontinuous in a repeating or non-repeating pattern around the circumference of the tubular section. If discontinuous cuts are aligned axially, they can form one or more additional axial spines 116 to bias bending and flexing planes of the catheter support tube 100. As a further example, if circumferentially discontinuous cuts are mixed and aligned with circumferentially continuous cuts, they can form a discontinuous axial spines.

A portion or portions of the support tube 100 can flare radially outward to form a seal with the inner diameter of an outer or intermediate catheter. In another example, a seal or flow restriction is not required and lumen between the inner diameter of the outer catheter and the outer diameter of the aspirating clot retrieval catheter 35 can be small enough for aspiration losses to be negligible. Alternatively, the catheter diameters can be sized so the lumen can be set so that aspiration is applied at two locations, both the distal end of the clot retrieval catheter and the distal end of the outer catheter.

In other examples, the tubular shaft of the catheter can be supplied without a support structure of struts, such that the tubular shaft is made solely from a polymeric section. For example, the catheter 35 can have a shaft formed from a single polymeric extrusion. The extrusion can be, for instance, fabricated from polyether ether ketone (PEEK), Polyimide, Polyethylene, or another rugged thermoplastic polymer. The surface of the extrusion can be laser cut and profiled with a series of ridges or recesses to afford enhanced torque, push, and trackability characteristics. The ridges or recesses can be applied by passing the polymeric extrusion through a heated profiling die that can melt and cool the tube as it is passed through. Prior to profiling, a composite tube can be utilized that has previously been reflowed to have a variable longitudinal stiffness profile and subsequently passed through the profiling die to impart a homogenous support structure as desired.

Where an outer jacket has been reflowed over a laser cut hypotube and into the spaces between the ribs 118, there may be material radially protruding at the location of the laser cut struts. The shaft can then be pulled through a sizing die to remove any excess material above the struts such that the overall outer diameter of the support tube 100 shaft is consistent for a reduced delivery profile.

The axial spine or spines 116 themselves can be formed or cut at various thicknesses. A thicker spine can provide more column strength and axial stiffness for better kink resistance and insertion and retraction performance of the catheter. Conversely, a spine of a thinner thickness can provide more flexibility in bending for navigating tortuous areas of the vasculature. The spine or spines can also taper in thickness along the length of its axis in order to incorporate both of these advantages. A tapered spine or spines can be made stiffer proximally for good pushability characteristics and very flexible distally to allow the tubular section to contort and twist around the vessel paths.

FIGS. 3a-3d illustrate an example support tube framework 110 tube with a single tapered spine 116 extending parallel to the longitudinal axis 111 of the support tube 100. The taper angle of the spine 116 may vary throughout the length of the tube framework 110. The spine can have at least a distal first width or thickness 136 which is less than a proximal second width of thickness 138, such as the case shown in FIG. 3c. The thickness of the spine 116 proximally can be thicker and stiffer than more distal sections of the support tube to provide good pushability, while the distal sections of the framework 110 can have a thinner, more flexible spine 116 to allow the framework to contort and twist around tortuous vessel paths.

Use of at least a single spine 116 as seen in FIG. 3b can reduce the possibility of elongation under tensile loads, such as when an enlarged catheter distal tip 42 is being retracted into an outer sheath or intermediate catheter. The ribs 118 of the framework 110 can terminate at opposing junction points 126 on opposite sides of the tapered spine 116. The ribs 118 can have varied strut widths and varied spacing densities between adjacent ribs to further optimize the stiffness profile of the support tube 100.

Another example of a support tube framework 110 having twin tapered spines 116 spaced 180 degrees apart is shown in FIG. 4a-d. Similar to FIG. 3, the spines can be tapered at various different angles along their length, or the taper can be a curve relative to the longitudinal axis 111 to transition the stiffness of the support tube 100 along its length. In general, the support tube 100 can be stiffer at the proximal end 112 and very flexible near the distal end 114 to ensure accessibility as near as possible to the target site of an occlusion.

Compared to a single spine, the use of additional spines 116 can give the framework 110 greater resistance to localized elongation between the ribs 118 when the support tube 100 is subjected to lateral and tensile loads. The disposition of the spines 116 of the tube diametrically opposed to each other (see FIG. 4b) can encourage bending of the framework 110 in a single plane 120 extending through the two spines (see FIG. 4a). This configuration, coupled with the opposing sets of junction points 126 for the ribs 118, can aid in delivering a balanced and consistent push or thrust force through the length of the catheter. Multiple spines also help the support framework resist longitudinal compression during deployment to ensure exact placement at a treatment site. The opposing spine arrangement can also prevent the framework 110 from bending either spine in a direction circumferentially normal to the spine, a direction more prone to kinks or potentially fracture in locations where the width of the spine strut can exceed its thickness.

Figure 5A:
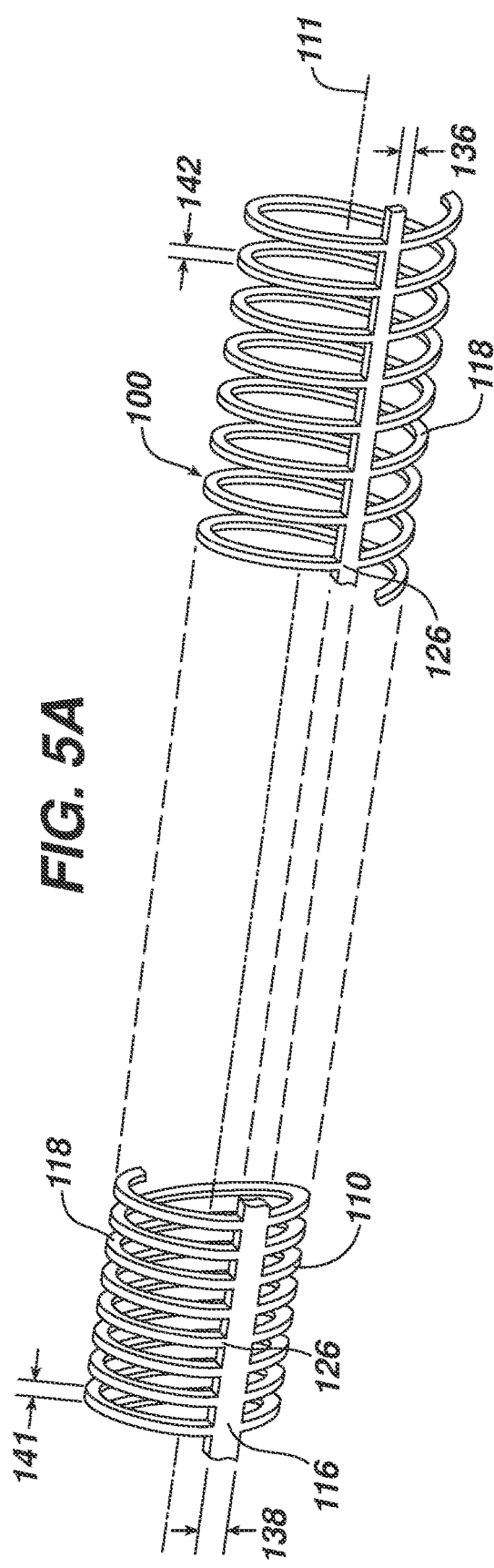
FIG. 5a shows another support tube with helical ribs according to aspects of the present invention.
Figure 5B:
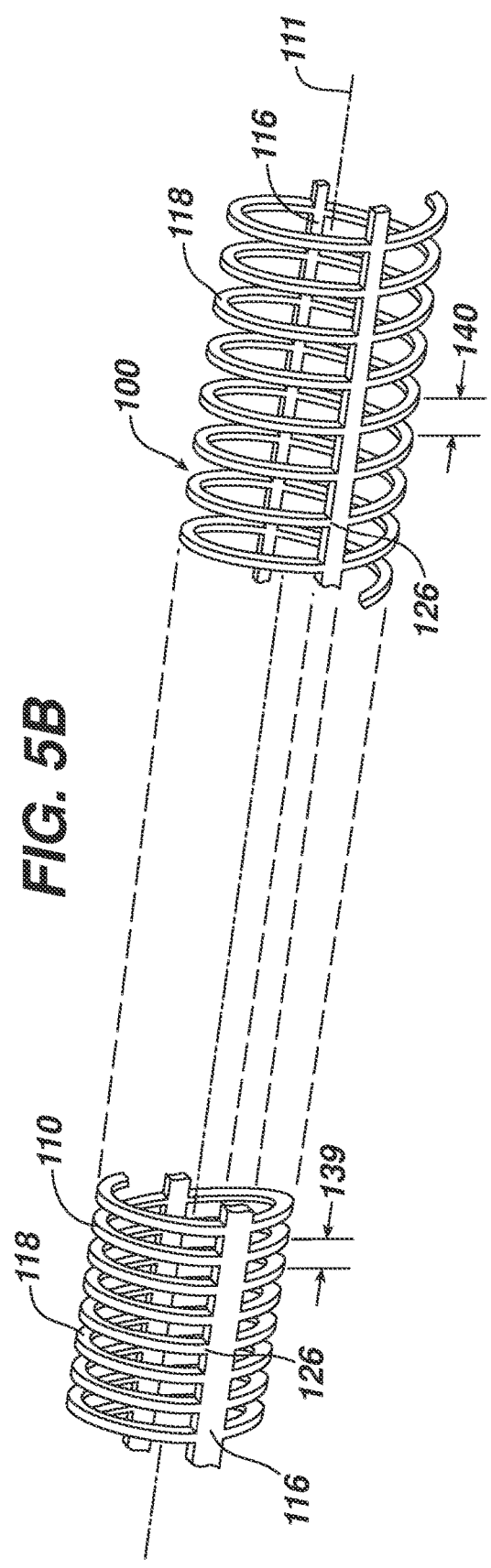
FIG. 5b illustrates another support tube with variable rib pitch according to aspects of the present invention.

In FIG. 5a-b, there is illustrated a support tube 100 in which the ribs 118 of the support framework 110 are arranged in a coiled helical configuration about the longitudinal axis 111 of the support tube 100. The coiled structure can be produced with an overlapping spine 116 as shown in FIG. 5a, or the structure can be formed integrally by laser cutting a single hypotube with ribs and spines. In a similar example, two spines 116 can be formed 180 degrees apart along the length of the coil, as in FIG. 5b. A helical configuration for the ribs 118 with two spines can mean the respective junction points 126 of a rib with the spines are axially offset on opposing sides of the support framework 110.

Similar to other disclosed examples, the pitch between ribs 118 can be varied to further optimize the stiffness profile of the support tube 100. Reducing the rib pitch and increasing the thickness of rib struts can each contribute towards adding stiffness to a given region of the tube, whereas increasing rib pitch and/or decreasing rib width can reduce the stiffness properties of a given section. For example, a more proximal rib thickness 141 can be greater than the thickness 142 of a more distal rib, or a proximal rib pitch 139 can be less than a distal rib pitch 140, to add additional flexibility to the distal portion of the catheter. Similarly, a more proximal spine width 138 can be greater than a more distal spine width 136 to yield the same effect.

The combination of the aforementioned support framework 110 parameters of the ribs 118 and spines 118 with variations in the outer jacket or membrane material hardness and/or thickness can be optimized to provide a catheter body with effective pushability, trackability, and torquability in various regions of the support tube 100 such that the catheter can be delivered along the most challenging vessel paths to reach remote target treatment locations.

Referring to FIGS. 6a-d, a support tube 200 can have a framework 110 with interrupted double spines 214 where adjacent linear segments of the spines are positioned 90 degrees apart and run parallel to the longitudinal axis 111 of the tube. This configuration can be formed by cutting a series of rounded radial slots 212 into alternating and opposing sides of a hypotube or other tube stock to form adjacent ribs 118 along the length of support tube 200. This design effectively has interrupted spines at 90, 180, 270, and 360-degree locations around the framework 110 which will allow the tube to bend in two perpendicular bending planes 120, 121 which are aligned axially to extend through each of the interrupted spines 214.

Having interrupted spines which define multiple bending planes can allow for a greater freedom of movement in three-dimensional vessel paths. However, such a design can have a reduced column stiffness and be prone to elongate axially under tension, such as when an expandable mouth of the catheter is retracted into an outer intermediate catheter. Expansion of the support tube can inhibit the mouth from collapsing down and exerting a better grip on a captured clot.

Other features can be incorporated to counteract this. For example, one or more separate and continuous wire spines (not shown) can be incorporated integrally with or separate to the support tube 200. Where separate, the outer polymer jacket or membrane can be used to fuse the hypotube support framework 110 and wire spines together. The wire spines can add integrity to the structure under tensile loading and prevent the tube from axially elongating when retracting a catheter tip 42 with an expanded mouth into an outer sheath of intermediate catheter. In another example, the width of the rib 118 struts can be increased to adjust the stiffness in a way which can prevent undesired elongation of the support tube 200.

Turning to FIGS. 7a-d, a support tube 100 can have a framework 110 with looped ribs 118 joined by a helical spine 117 extending between the proximal end 112 and the distal end 114 of the framework. A similar design is illustrated in FIGS. 8a-d, where two helical spines 117 extend out-of-phase with each other 180 degrees apart. Helical spines allow the support tube 100 to twist about the longitudinal axis 111 along the length of the tube.

As is the case with interrupted spines, helical spines may also tend to straighten and elongate when support tube 100 is subjected to tension. To prevent elongation, the pitch of the helix can be increased to where the twist is very gentle and, locally, the spine or spines are nearly straight. For example, a pitch between 10 mm and 200 mm can be used, more preferably between 50 mm and 100 mm.

A compound design can have a support framework 110 where a helical spine or spines 117 merge with sections of the framework where the spine or spines are straight relative to the axis 111. Regions of the support tube 100 with more flexible outer covers or jackets (not shown) can be aligned with the straight spines to reduce the likelihood of tensile elongation.

Where a helical spine 117 can have junction points 126 which form acute angles with the respective ribs 118, cutouts 128 can be made with large edge radii as shown in FIG. 8e. The cutouts 128 can locally relieve strain at the junction points 126 as the support framework 110 twists about the longitudinal axis 111.

Various views of another example of a support tube 300 are shown in FIG. 9a-e. The support tube 300 can have substantially tubular section, such as a hypotube or polymeric extrusion, with a pattern of cuts forming radial slots 312 spaced around a longitudinal axis 111. The interruptions can be sequenced so the discontinuities in the cuts align axially to form one or more continuous spines 314. In one example, the radial slots 312 form two continuous axial spines 314 spaced 180 degrees apart to maintain a smooth stiffness profile on alternate sides of the support tube 300.

In one example, the cuts forming the radial slots 312 can be completely circumferential around the support tube 300. Sections around the circumference of the tube can incorporate geometric features which form a keyed interface to interlock with adjacent axial sections such that longitudinal and torsional loads can be transmitted without the use of spines. The keyed interface can be a dovetail or similar arrangement, so the support tube body fits together like a puzzle. In a similar example, the keyed joints can be maintained but the radial slots 312 can be cut with discontinuities to form continuous or discontinuous spines for circumstances where additional pushability is desired.

Figure 9A:
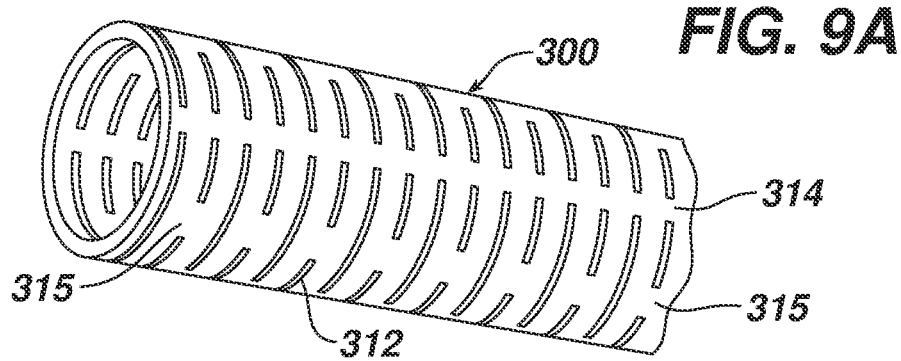
FIG. 9a-d are a series of views of another support tube with radial slots according to aspects of the present invention.
Figure 9E:
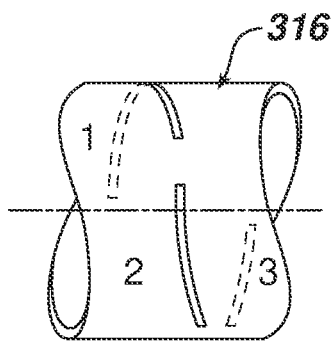
FIG. 9e is a representation of the cuts per revolution for the radial slots in a support tube according to aspects of the present invention.
Figure 9D:
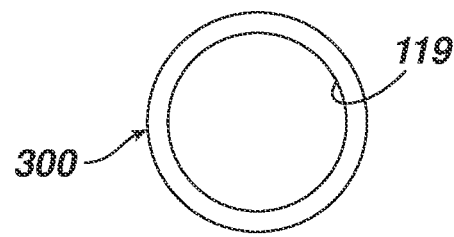
Figure 9B:
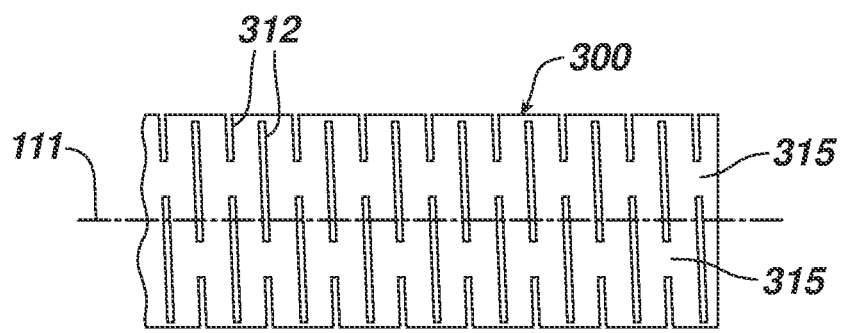
Figure 9C:
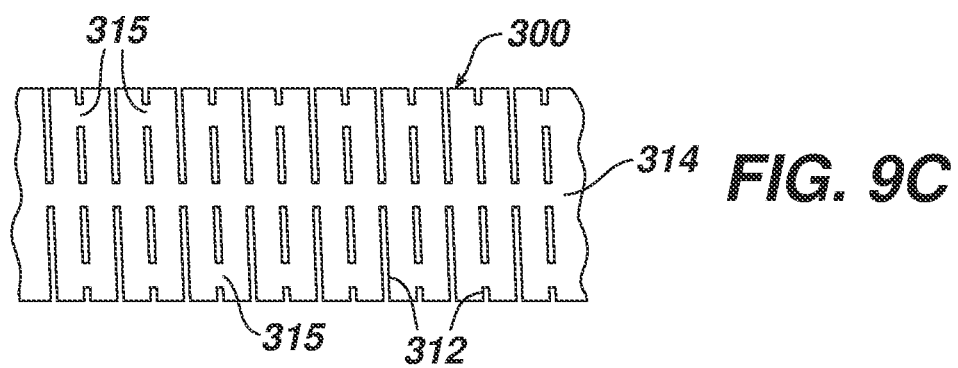

In some cases, the radial slots 312 can be in a helical configuration and include interruptions in an alternating pattern such that they form an interrupted spine or spines 315 which are angularly offset from the one or more continuous spines 314, as seen in FIG. 9b and FIG. 9c. In this way, the helix cut pattern can include one or more radial cuts per rotation 316 about the longitudinal axis 111. In the example shown in FIG. 9e, three cuts per revolution are utilized. Each of the cuts or radial slots 312 can be cut at a constant length, or variable lengths can be used so that lateral flexibility of the support tube 300 can be provided in multiple planes. By patterning the radial slots 312 to incorporate both continuous spines 314 and interrupted spines 315 the potential for elongation of the support tube 300 in tension can be minimized.

Figure 10A:
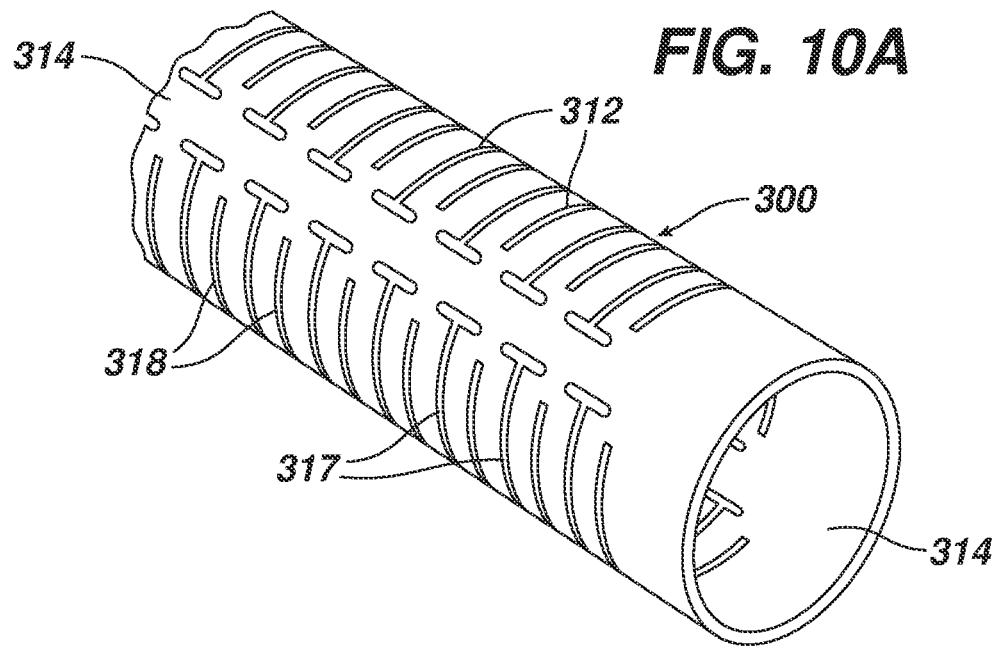
FIG. 10a-b are two views of another support tube with radial T-slots for strain relief according to aspects of the present invention.
Figure 10B:
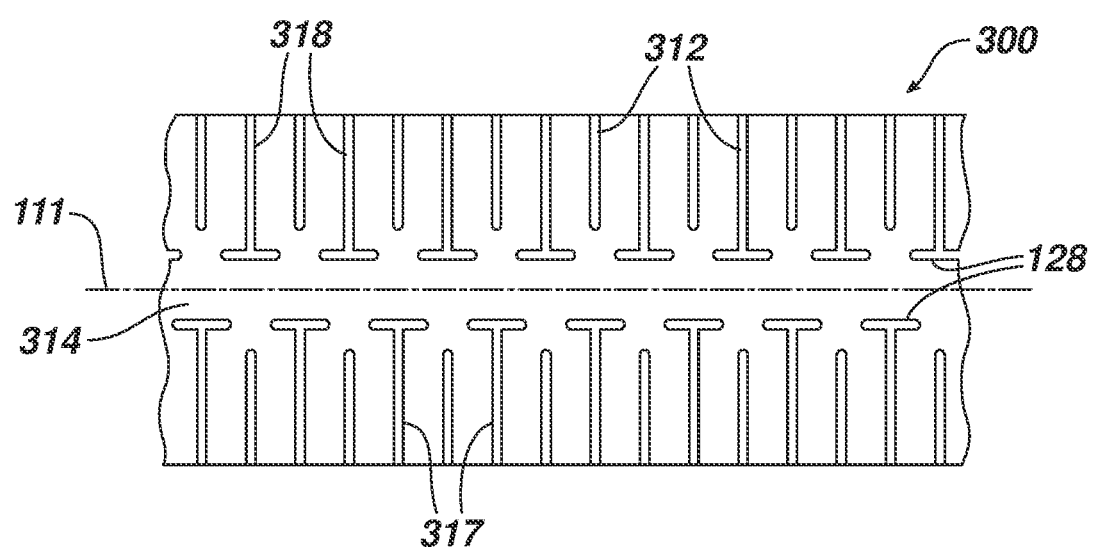

Another support tube 300 with a hypotube or polymeric extrusion having radial slots 312 cut into the tubular section is shown in FIG. 10a-b. The cuts can be planar with the transverse axis on alternating sides of the support tube 300. The radial slot 312 cuts can terminate or transition to a transverse cut, forming an "I"-shaped or "T"-shaped pattern defining one or more continuous axial spines 314. The transverse cuts of the pattern can serve as a strain relief cutout 128 feature, which can vary in thickness and increase the free length of the spine or spines so that the support tube 300 can flex more easily about the bending planes. The I-slots 316 and T-slots 317 can alternate in an offset pattern on either side of to form two continuous spines spaced 180 degrees apart, as pictured in FIG. 10b. Two continuous spines can allow the support tube 300 to maintain significant longitudinal stiffness along the axis 111.

Figure 11A:
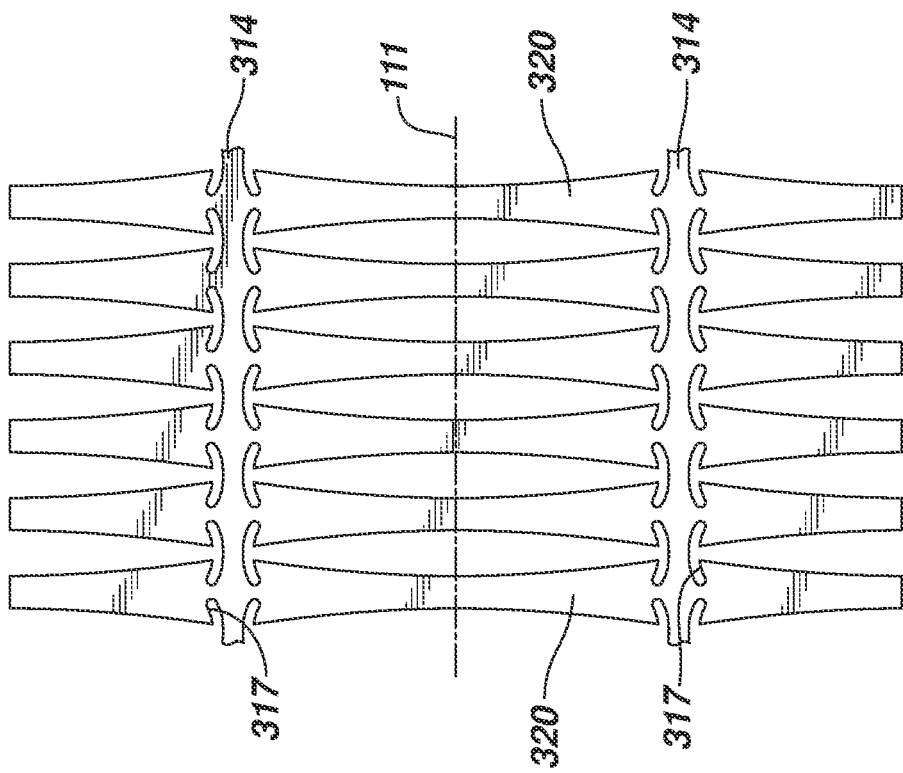
FIG. 11a is a flat pattern of an example support tube with T-slots and contoured ribs according to aspects of the present invention.
Figure 11B:
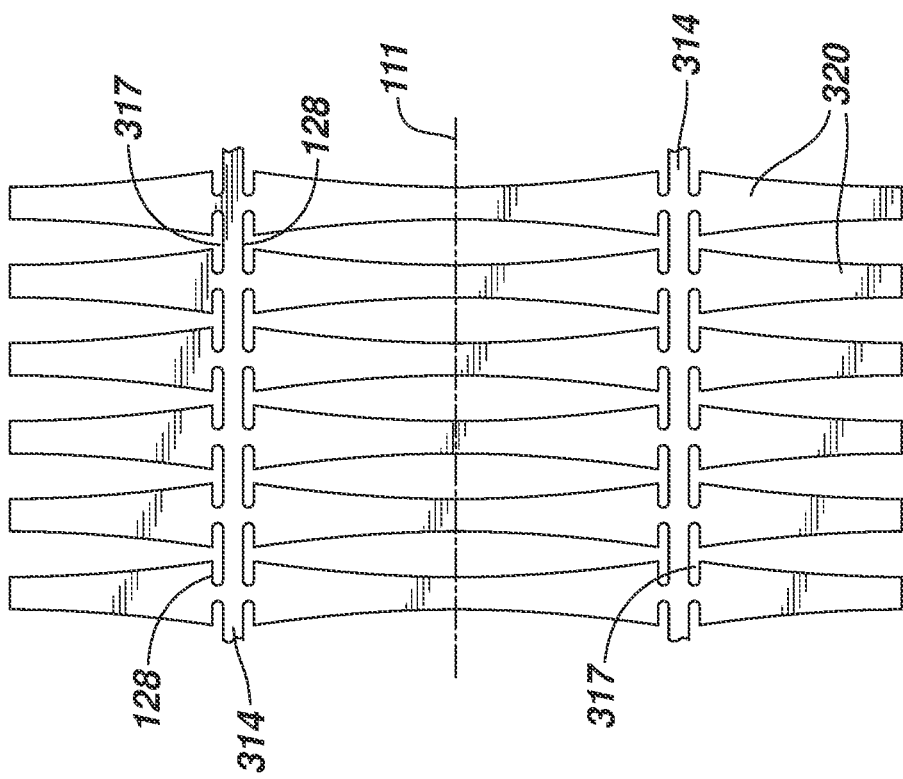
FIG. 11b is a flat pattern of another example support tube with T-slots and contoured ribs according to aspects of the present invention.

Flat patterns showing variations of support tube 300 with T-slots 317 and strain relief cutouts 128 are illustrated in FIG. 11a and FIG. 11b. The T-slots 317 can be cut at an angle, or with curves as shown in the figures, such that the formed members are contoured ribs 320 which vary in thickness about the longitudinal axis 111 of the tube. The contoured ribs 320 can be a wider width near the opposing continuous spines 314 and narrow to a thinner width in mid-span between the spines, as seen in FIG. 11a. This arrangement offers a greater space for the ribs 320 to move in bending while offering additional support for the tube 300 against the vacuum pressure under aspiration.

In another example, the strain relief cutouts 128 of the ribs 320 can be T-slots 317 with a gentle curve or radius at the spines 314 like those of FIG. 11b. While offering additional space for the contoured ribs 320 to bend proximally or distally relative to each other in tortuous vessels, curved T-slots can give additional flexibility to the support tube 300 by promoting bending in directions tangential to the curve.

FIG. 12a-d illustrate another example of a support tube 100 which can have a framework 110 machined from a tube where a single axial spine 116 anchors a plurality of ribs 118 extending between a proximal end 112 and a distal end 114. The spine can have at least a distal first width or thickness 136 which is less than a proximal second width of thickness 138 to provide good pushability to the framework 110 proximally and a more flexible spine distally to contort and twist through vessel paths.

The ribs 118 can be cut an angle 130 so that the free ends extend distally to the junction points 126 of the ribs with the spine 116. Although angled, the ribs 118 can maintain a circular inner lumen 119 (as seen in FIG. 12d) and outer diameter. This arrangement allows the ribs 118 to move proximally relative to the spine 116 when compressed between the junction points 126 and a firm clot that resists being stretched into the nominal resting inner diameter of the framework 110. This compressive force transmitted to the most distal rib can be transmitted proximally to adjacent ribs by the outer cover and/or jackets (not shown) disposed around or encapsulating the framework. The jacket can be reflowed to the cut support framework 110 so that it sits between and transmits longitudinal loads between adjacent ribs 118. The jacket can also be polymeric so that it has the elasticity to stretch and expand in diameter in response to movement of the ribs. Compressive forces from a clot can cause the cross-sectional area of the lumen 119 to increase as the ribs move proximally to a position where the rib angle 130 is more perpendicular to the spine 116 and longitudinal axis 111 and the elastic jacket expands radially outward, temporarily increasing the reception space available for clot capture.

An illustrative example of how a support tube 100 similar to that of FIG. 12a-d can further be tailored for more optimal delivery characteristics is indicated in FIG. 13a-d. A variable-width spine 116 can link variable-stiffness sections of the support tube, where a proximal rib pitch 139 of the ribs 118 in a more proximal axial section is greater than a distal rib pitch 140 in a more distal axial section. The spine 116 can have a first spine width 136 near the distal end 114 of the support framework 110 less than a second spine width 138 near the proximal end 112, thereby increasing the distance between respective junction points 126 between the spine and the ribs 118. It can be appreciated that the spine can taper to other intermediate widths between the first and second widths. The ribs themselves can also be cut at various thicknesses within different axial sections of the support framework 110 as desired or can be formed with different thicknesses at various clocking positions around the longitudinal axis 111.

Figure 13A:
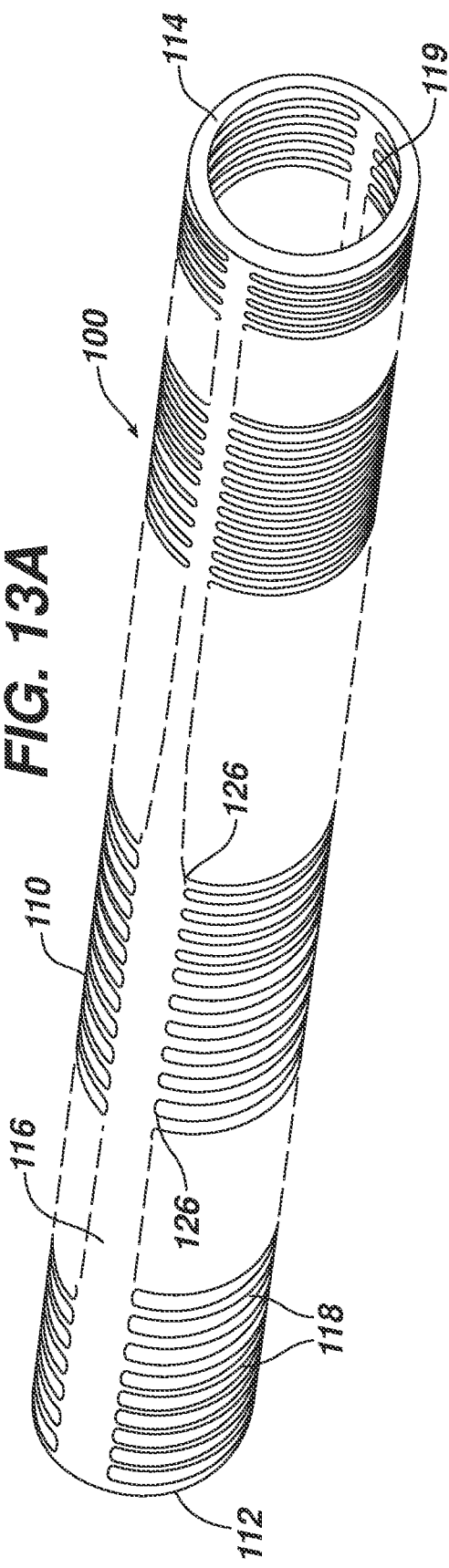
FIG. 13a-d are a series of views of another support tube according to aspects of the present invention.
Figure 13B:
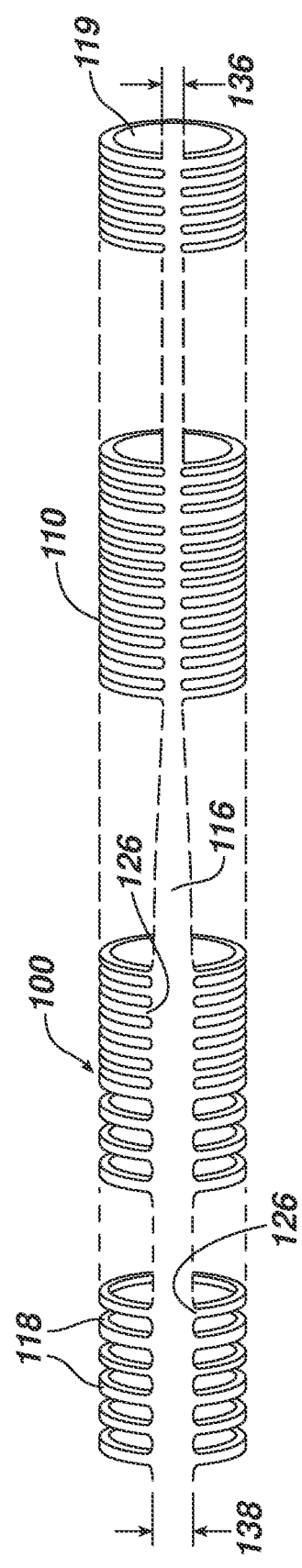
Figure 13C:
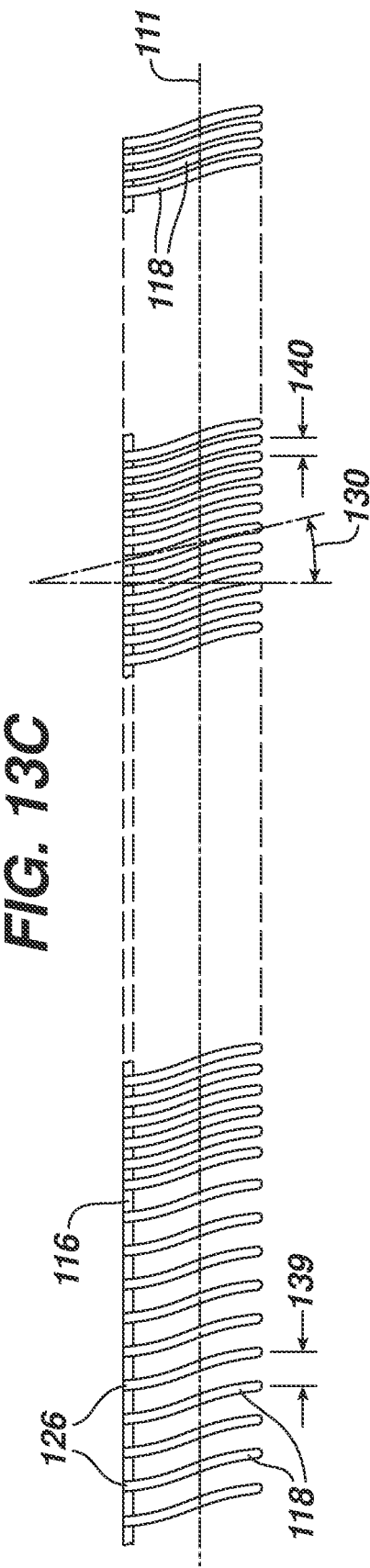
Figure 14:
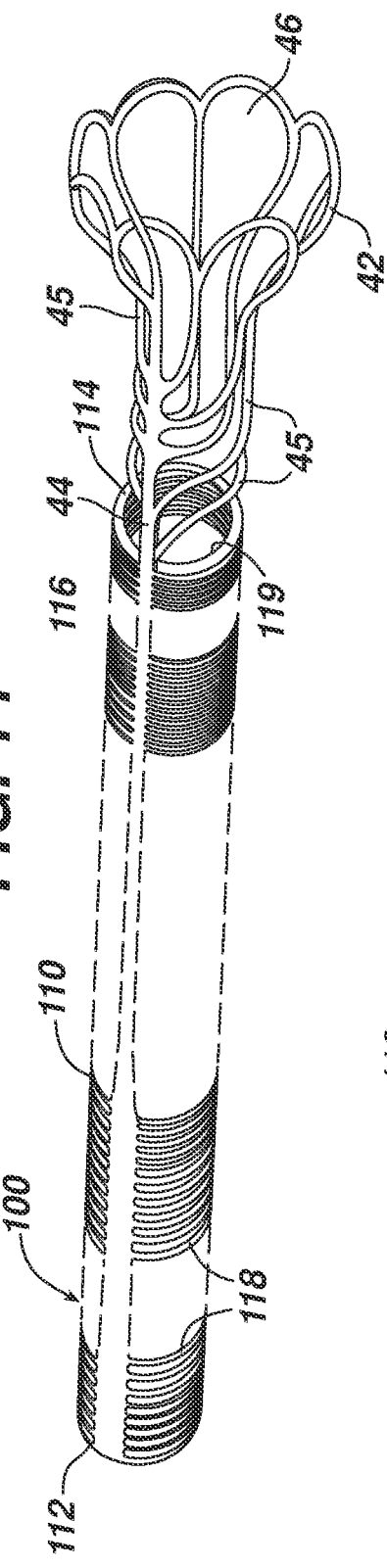
FIG. 14 shows an expanded distal tip of the catheter connected to the support tube of FIG. 13a according to aspects of the present invention.
Figure 13D:
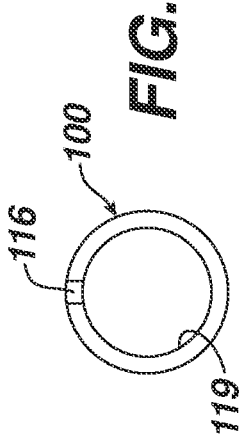

A support tube 100 similar to the example of FIG. 13a is shown connected at the distal end 114 to a self-expanding catheter tip 42 framework in FIG. 14. The struts of this framework can be formed from Nitinol or another shape-memory material with sufficient elastic strain capacity such that the elastic limit would not be exceeded when the tip is constrained and delivered in the collapsed configuration within an outer catheter. Additional frameworks of wire or non-superelastic materials can also be envisaged, where a lower degree of strain is required to move from a collapsed state for delivery to an expanded state for clot retrieval.

The spine 116 of the support framework 110 can transition directly into a spine extension 44 strut or struts at the distal end 114, and the spine can be integral with the extension (e.g., cut from the same hypotube) such that the stiffness profile of the catheter is smoother and weak transitions can be eliminated. Supporting arms 45 of the expansile tip 42 can extend distally from central junctions with the spine extension 44, or one of more of the arms can be connected with the distalmost rib of the support framework 110. The arms can be connected with other struts or themselves can include radial curves to form the circumference of the enlarged distal mouth 46 of the catheter tip 42. The support arms 45 can be arranged so that they expand radially outward as a clot is being aspirated or, for example, when a thrombectomy device is being retracted through the mouth 46 for a higher success rate when targeting stiff clots.

The support ribs 118 of the support tube 100 can be formed at an angle relative to the axis of the tube so the ribs are substantially cylindrical in profile but do not have a planar cross-section. In cases where the support arms 45 of the tip 42 do not connect directly to the most distal rib, the free ends of the ribs 118 can move proximally relative to the longitudinal spine 116 when under compressive loads, such as during clot retraction. Proximal movement of the ribs 118 can have the effect of expanding the inner diameter of the catheter lumen 119 locally as the clot is retracted through the support tube. An elastomeric outer jacket or membrane covering the support framework 110 and expansile tip 42 can be configured to allow the support arms 45 and ribs 118 to expand under these compressive loads.

An example of a support tube 100 having a tubular support framework 110 where axially curved ribs 118 are spread between two continuous spines 116 spaced 180 degrees apart is shown in FIG. 15a-d. The ribs 118 can have proximal peaks 136 defining a most proximal point where the ribs intersect the spines 116 at the junction points 126. The profile of the ribs 118 beyond the junction points 126 can take on a gently undulating non-planar cross-section which can have one or more curves, but still defines a substantially cylindrical catheter lumen 119. As seen isometrically in FIG. 15a, the rib profile can have a first proximal curve 132 radially offset from the proximal peak 136 and a second distal curve 134 radially offset from the proximal curve and culminating in distal peak 138, so that at least a portion of the ribs is distal to the connection at the junction points 126. It can also be appreciated that the corresponding junction points 126 with each spine 116 can also be axially offset proximally or distally to the opposed junction point with the other spine. Ribs 118 that form a substantially cylindrical profile but do not have planar cross-sections have the ability to expand in compression during retraction of a clot from a blood vessel to the inner lumen 119 of the catheter, thereby allowing this configuration of the support framework 110 to "swallow" dense clots that may otherwise be restricted from entering a non-expandable form.

Figure 16:
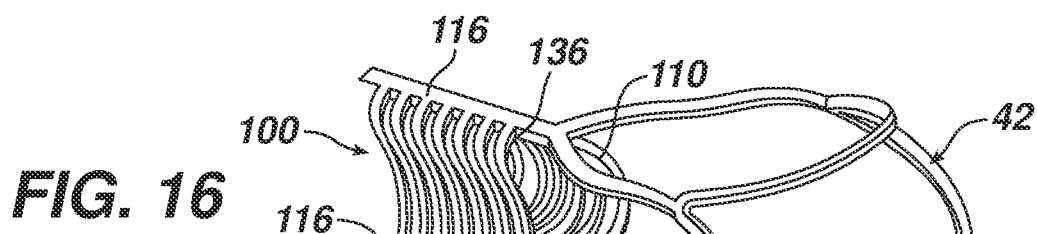
FIG. 16 shows an expanded distal tip of the catheter connected to the support tube of FIG. 15a according to aspects of the present invention.
Figure 17A:
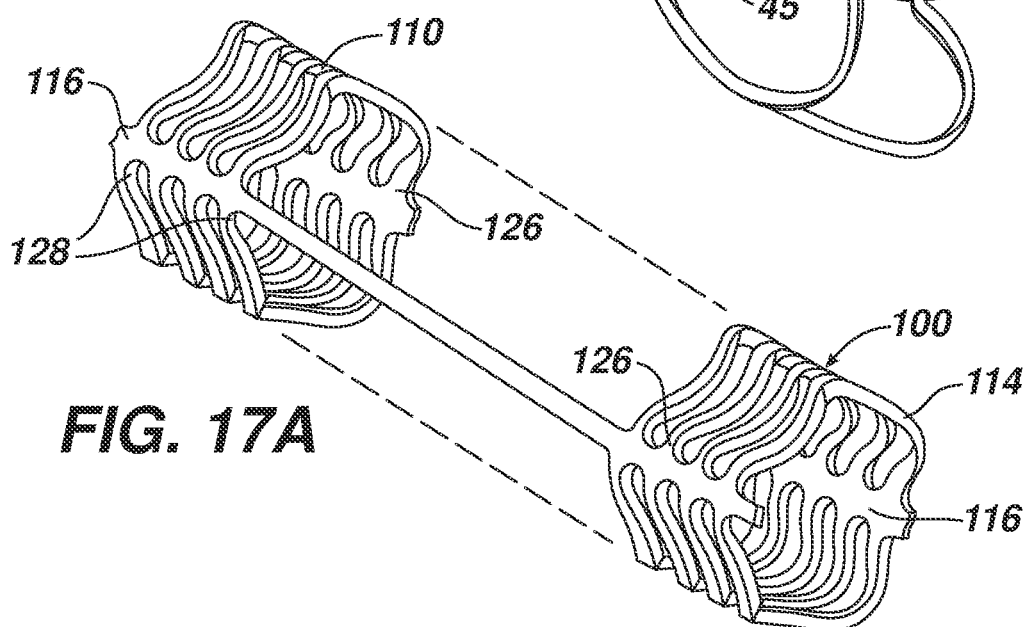
Figure 17B:
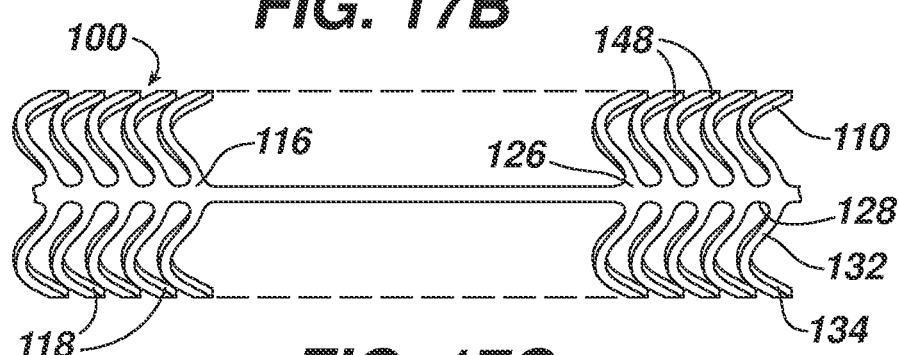
Figure 17C:
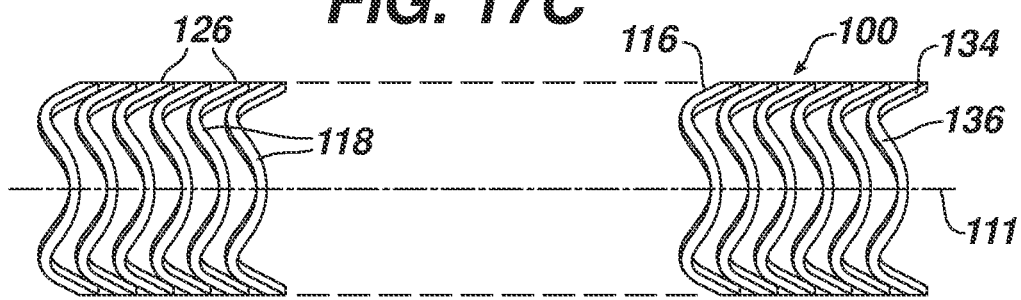

The support framework 110 with ribs 118 having one or more axial curves can be arranged with the spines 116 connected in-line at the distal end 114 with the support arms 45 of an expanding catheter tip 42 framework, as illustrated in FIG. 16. Connecting the arms 45 in-line with the spines 116 allows for the advancement forces to be transmitted directly along the spines to the support arms for enhanced pushability when the catheter is being advanced through an outer intermediate catheter. This configuration also allows the distal peaks 138 of the ribs to be kept free so that frictional and compressive forces generated between the support framework 110 and an outer catheter during advancement, due to the expansile tip pressing radially outwardly against the outer catheter, are not transmitted in a direction which would cause the ribs to expand. This expansion can otherwise negatively affect deliverability by having at least a portion of the support tube 100 pressing against the inner surfaces of the outer catheter, generating increased friction.

A support tube 100 having a support framework 110 similar to that of FIG. 15a-c but with ribs 118 extending in a wave pattern circumferentially can be seen in FIG. 17a-d. The ribs 118 can intersect with two offset spines 116 spaced 180 degrees apart in a substantially perpendicular fashion at the junction points 126. The proximal curve 132 and distal curve 134 of each rib can therefore form a proximal peak 136 that is circumferentially offset from each spine 116. The distal peak 138 of the ribs can be kept free to allow the ribs to flex individually. The wave pattern generates more contact points between the ribs 118 and an outer jacket or membrane to distribute forces more evenly across the circumference while still maintaining the ability to expand in compression. It can also be appreciated that the strut width of the ribs and spines can be varied, and the corresponding junction points axially offset at each spine to further tune the movement of the ribs 118 and the stiffness profile of the support framework 110.

FIG. 18a-d shows a case where the ribs 118 of the support framework 110 can have proximal curves 132 and distal curves 134 bending in opposing directions to those of the ribs in FIG. 17a-d. Undulations in the ribs of the support tube can allow the tube to expand so that stiff clots that cannot be compressed into the nominal resting internal diameter of the device can instead be retrieved by the radial expansion of the support framework 110 which can occur when aspiration is maintained on an otherwise lodged or incompressible clot. Similar to other examples, the outer jacket or membrane covering the support framework 110 can be made of an elastomeric material so that the support tube is not restricted from expanding. The use of twin spines 116 in the examples where the ribs have a circumferential undulations or wave patterns can provide better pushability than a single spine while preventing the support tube 100 from elongating under tension when an expandable tip 42 is being drawn proximally into an outer intermediate catheter.

Further features which aid in the movement of the ribs 118 and the overall flexibility of the support framework 110 can include enlarged openings or cutouts 128 at the junction points 126 of the framework. Cutouts 128 increase the movement capability of individual ribs with respect to the spine or spines 116 while providing strain relief at the interface. A highly flexible catheter can reduce the risk of cracking or ultimate fracture by reducing the geometric stress concentration at the junctions through strain relief cutouts 128. Cutouts 128 at the junction points 126 also encourage the ribs to flex independently to better accommodate the loads of a procedure.

Figure 19A:
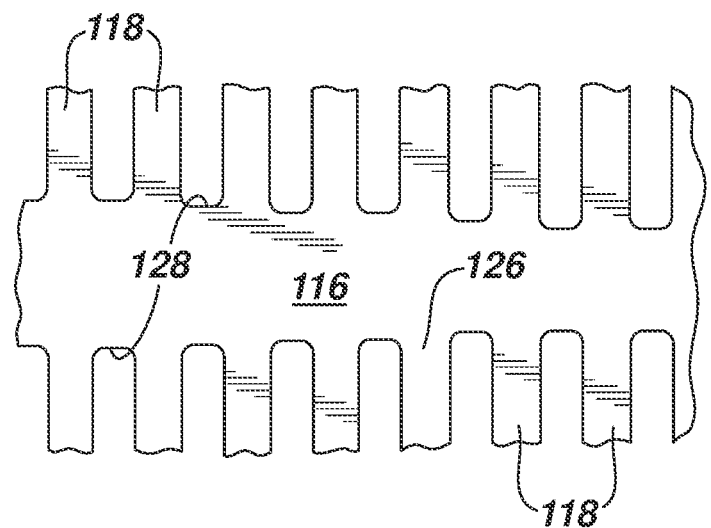
FIG. 19a-c illustrate various possible strain relief cutouts according to aspects of the present invention.
Figure 19B:
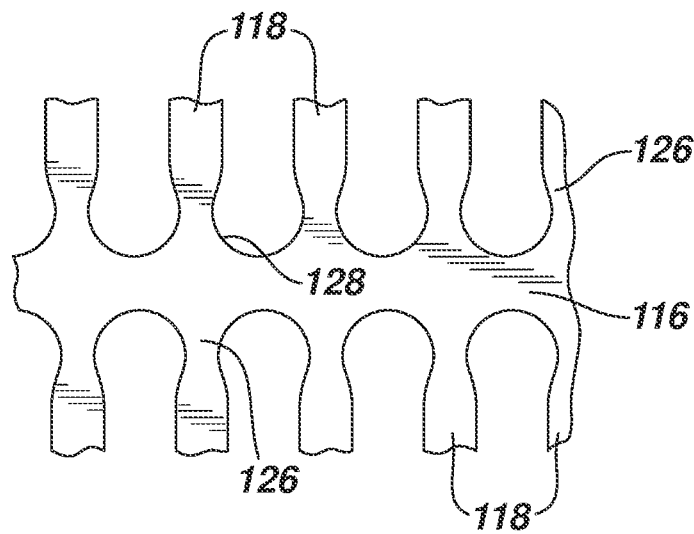
Figure 19C:
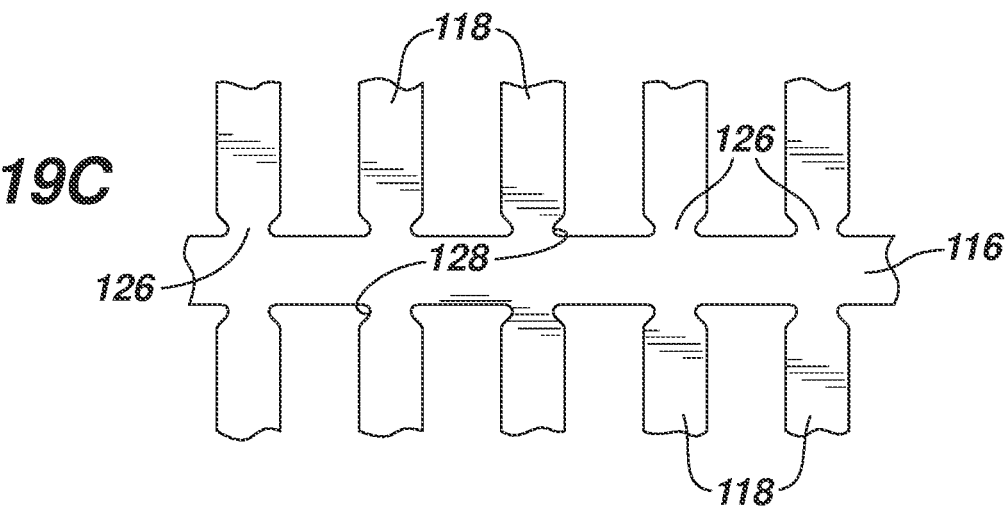

Various additional geometries of strain relief cutout patterns can be seen in FIG. 19a-c. These features can be introduced in a support tube 100 that is a hypotube by incorporated an additional machining step to the rib cuts or can be cut or formed integrally when the support tube is extruded or injection molded. Depending on flexibility preferences in a particular axial segment of the tube support framework 110, a user can introduce beveled or rounded strain relief cutouts 128 to the corners of the junction points 126, as in FIG. 19a. Such a cutout can be particularly useful in situations where the rib space is very dense and there is insufficient room for other stress reducing geometries. When the rib pitch is greater, a cutout 128 at the junction points 126 with an enlarged, more generous radius can be used to reduce stresses further, as illustrated in FIG. 19b. Similarly, fine rib spacing can be retained by adding smaller relief cutouts 128 to the corners of the junction points 126, as in FIG. 19c.

To improve multiaxial flexibility of the support tube, it is often advantageous to minimize the overall number of connections to the spine or spines. FIG. 20a-c illustrates several examples where a support tube 100 has a support framework 110 in which a series of supporting ribs 118 merge into a single spine connector 146 for connections with one or more spines 116. Each set of support ribs may comprise one, two, three, or more ribs 118. In FIG. 20a, a pair of ribs 118 have opposing wing segments 147 which curve or taper centrally into a spine connector 146 joining to spine 146. By connecting support ribs 118 in sets that have a single connection to the one or more spines 116 a longer length of spine is free to bend for a given density of ribs. A similar concept with three ribs 118 joining into a single connection is shown in FIG. 20b. The outer ribs of the set can have wing segments 147 to merge with the central rib, which can have a direct connection with the spine connector 146.

A series of supporting ribs 118 can merge into opposing spine connectors 146 for connections with twin spines 116 spaced 180 degrees apart as shown in FIG. 20c. Additional spine can also be envisioned. Opposing twin spines can provide better pushability than a single spine while preventing the support tube 100 from elongating under tension, such as when an expandable tip 42 is being drawn proximally into an outer catheter. Fewer connections with the spines can give the framework 110 better flexibility to bend along the bend plane passing through the longitudinal axis 111 and each of the spines 116.

Figure 21A:
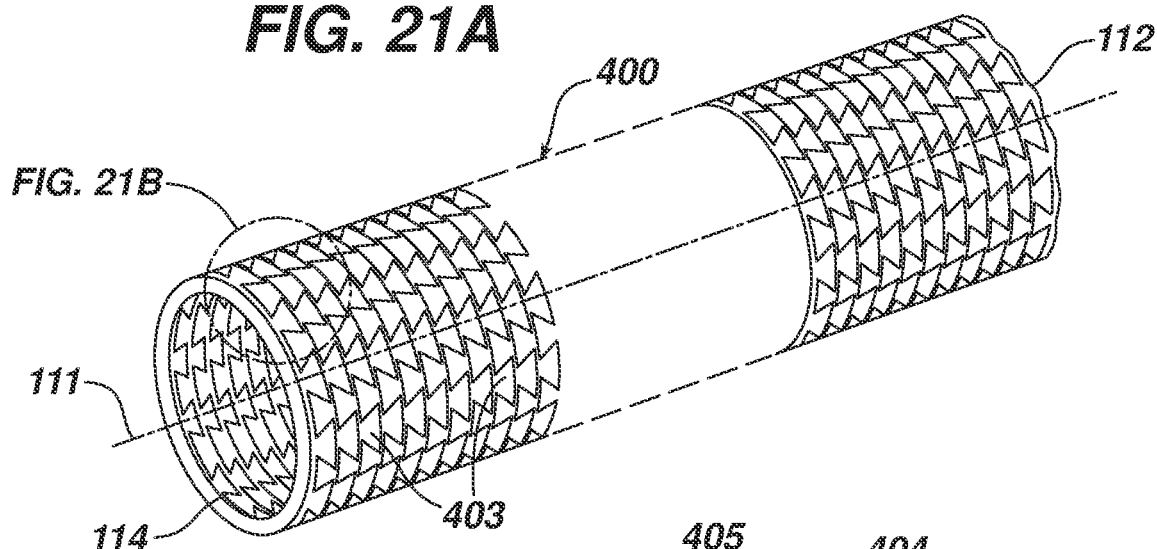
FIG. 21a shows a puzzle cut support tube with rings joined by interlocking features according to aspects of the present invention.

A further example of a support tube 400 having a different configuration where radial slots create a puzzle-cut pattern is illustrated in FIG. 21a. The puzzle cut tube can be substantially a series of interlocking ribs or rings 403. As each ring 403 is not integral with adjacent rings either proximally or distally, the puzzle cut tube can twist about the longitudinal axis 111, A puzzle cut support tube 500 construction can also resist tensile elongation due to engagement of adjacent interlocking features 404, 405. Distal interlocking features 405 can engage a particular ring with the next distal ring, while proximal interlocking features 404 can engage with the next proximal ring.

Figure 21B:
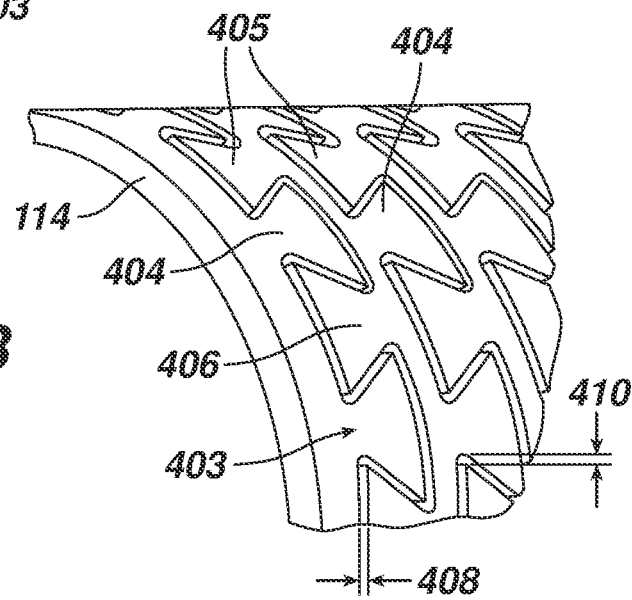
FIG. 21b shows a closer view of the features of the support tube of FIG. 21a according to aspects of the present invention.

Flexibility of the puzzle cut support tube 400 can be varied by increasing or decreasing the size of the ligament 406 between the interlocking features of the rings 403. FIG. 21b illustrates how the flexibility can also be varied by altering the number, shape and/or spacing of the interlocking features 404, 405. The longitudinal spacing 408 and circumferential spacing 410 between adjacent rings 403 can be controlled through the thickness of the cuts or through machining operations. The support tube can thus lengthen by the sum of the spacings 408 distributed longitudinally. Similarly, allowable twist can be adjusted by altering the circumferential spacing 410. The twist properties offered by a puzzle cut design for the support tube will aid in the catheter bending and torqueing in multiple planes as it is advanced through tortuous vascular paths.

Figure 21C:
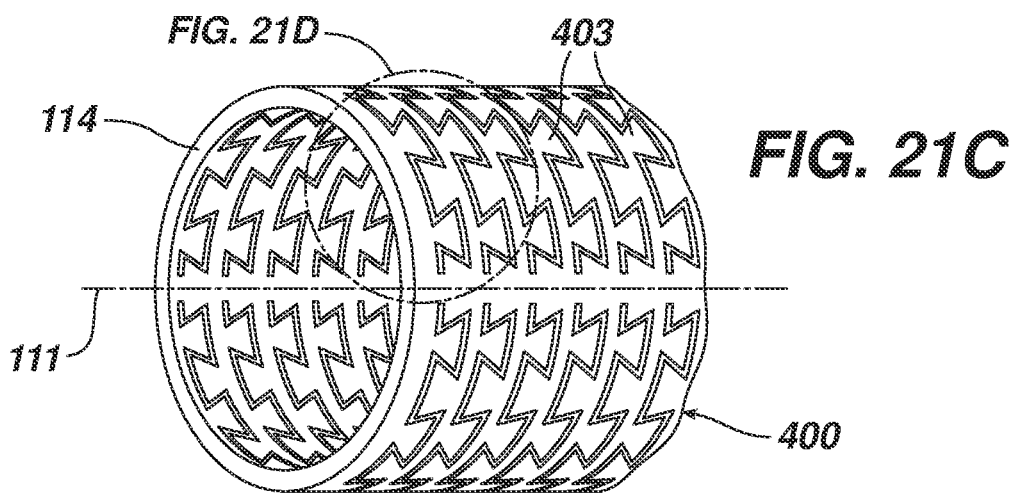
FIG. 21c illustrates another puzzle cut support tube with rings joined by interlocking features and a single spine according to aspects of the present invention.
Figure 21D:
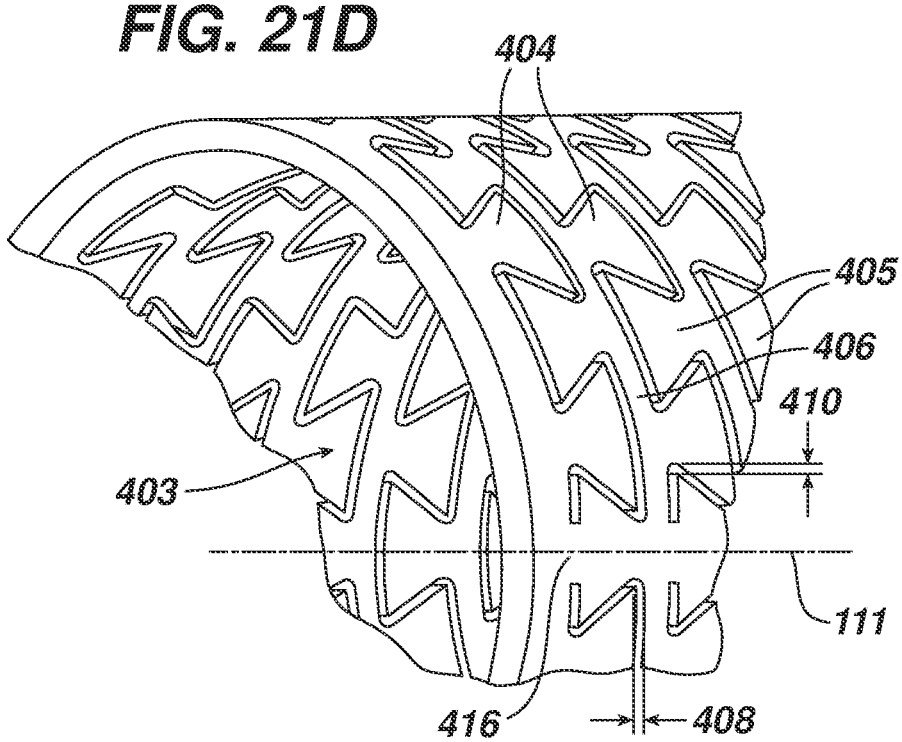
FIG. 21d shows a closer view of the features of the support tube of FIG. 21c according to aspects of the present invention.

FIG. 21c and FIG. 21d show how a support tube 400 can have a puzzle cut design with interlocking features while incorporating a longitudinal spine 416. A spine 416 can be added by aligning interruptions in the puzzle cut radial slots such that the rings 403 are fixed longitudinally at the spine, as seen in FIG. 21d. It can be appreciated that segments of the spine 416 can also be circumferentially offset, or the thickness of the spine can be different at various axial positions along the length of the support tube 400. The addition of a longitudinal spine 416 will help prevent the puzzle cut tube from lengthening under tensile loads. Additionally, a single spine will have minimal impact on the ability of the puzzle rings 403 to twist, so the catheter support tube can maintain its trackability advantages.

Figure 21F:
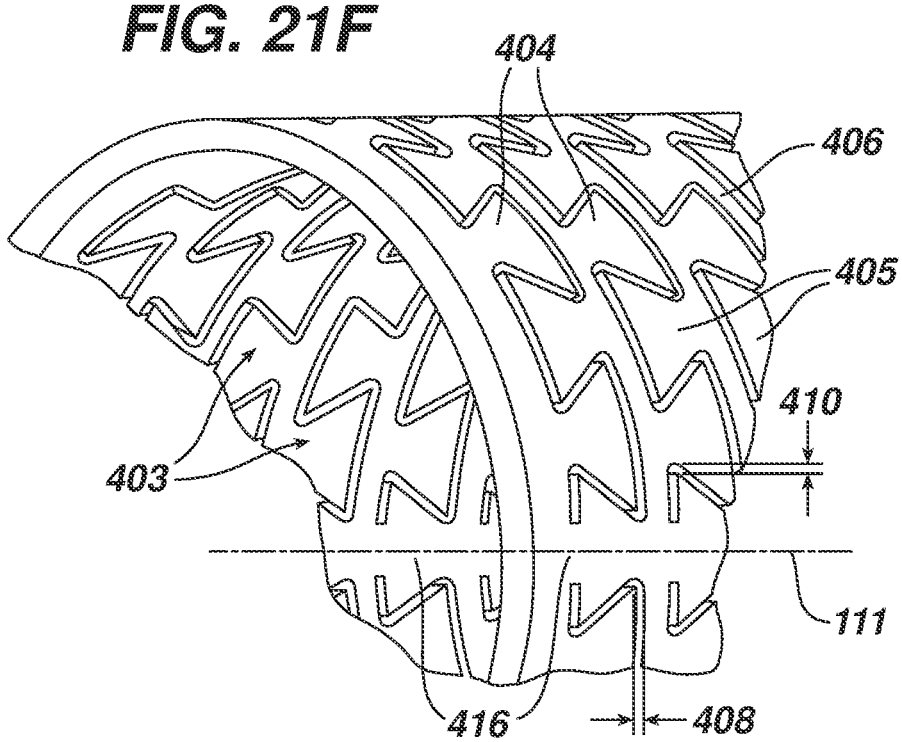
FIG. 21f shows a closer view of the features of the support tube of FIG. 21e according to aspects of the present invention.

Referring to FIG. 21e and FIG. 21f, a puzzle cut support tube 400 can incorporate two longitudinal spines 416 spaced 180 degrees apart. The addition of two spines 416 will prevent the support tube from lengthening under tensile loading and impart a preferred bending plane on the tube. If aligned parallel to the longitudinal axis 111 as shown, twin spines spaced 180 degrees apart will have minimal impact on the ability of the puzzle rings to twist, and the twist will change the preferred bending place of the tube to a degree controlled by the designed twist so that the support tube is capable of self-adjusting as it is advanced through tortuous vessels.

In another example, a support tube 500 can have a metal and/or polymer strand or wire construction formed into a braided or coiled structure 510, as shown in FIG. 22a. The strands 511 of the braided pattern 510 can form a radial array as a continuous structure in order to approximate a singular body support piece and be of sufficient density to support an outer membrane, similar to that of a laser-cut hypotube. The strands 511 of the support tube 500 can be formed on a straight mandrel so that a portion or portions of the tube flare radially outward to form a seal with the inner diameter of an outer or intermediate catheter.

Braided structures are known in the art to offer good flexibility in order to optimize the performance of catheter tubing. However, under tension, braids can tend to lengthen and reduce in cross-section diameter, while under compression, braids can expand in diameter and shorten. In the disclosed design of FIG. 22b, one or more interwoven spines 516 can be incorporated with the braid. The spine 516 will prevent the braided pattern 510 from elongating in tension or shortening in compression. Alternately, one or more spines 516 may be overlaid on top of the braided pattern 510 for simpler manufacturer. The spine 516 can be tacked in place with adhesives or other suitable method.

This expansion can be achieved by changing the size, orientation, or other properties of the strands 511 of the pattern 510. Further flexibility can be gained by altering the braid angle 512 or picks per inch (PPI) of the pattern. The braid angle 512 of the strands 511 and the density of the pattern can be chosen for the preferred axial and transverse mechanical properties of a given section of the support tube 500. For example, the braid angle and/or PPI can be different in a more proximal portion of the support tube, giving the proximal portion better pushability and torque response than a more flexible distal portion.

In one example, the braid angle 512 can be less than 90 degrees and over 20 degrees so that there is freedom for the support tube 500 to longitudinally compress. Maintaining the braid angle closer to 90 degrees will give the framework more flexibility than braid angles closer to 20 degrees, as the wires or strands of the 20-degree braid will be dispositioned in a more longitudinal direction. A braid angle 512 of greater that 90 degrees can also expand but to a lesser degree due to the denser spacing between braid strands 511.

Similar to other examples, the braid pattern 510 can have an elastomeric outer cover or jacket (not shown). The jacket can be reflowed to the outer surface of the braided tube or made to encapsulate the strands 511. Reflowed jacket materials will fill the voids between the braided pattern 510 and spine 516 further dampening the expansion or contraction of the tube. Encapsulating the pattern 510 with a reflowed polymer jacket can also help hold the braid and spine(s) 516 together. The jacket can be impermeable, or alternatively the braided or coiled pattern 510 can be of sufficient density so that fluid flow is substantially impeded between the exterior and interior of the support tube, such that an impermeable cover or seal is not necessary.

Any of the herein disclosed support tubes for clot retrieval catheter designs can be used in conjunction with a mechanical thrombectomy device. The combination of mechanical thrombectomy with aspiration through a funnel-like tip section can increase the likelihood of first pass success in removing a clot. During thrombectomy, a funnel-like shape of the tip section can reduce clot shearing upon entry to the catheter, arrest flow to protect distal vessels from new territory embolization, and also direct the aspiration vacuum to the clot face while the mechanical thrombectomy device will hold a composite clot (comprised of friable regions and fibrin rich regions) together preventing embolization and aid in dislodging the clot from the vessel wall. The shape of the tip can also aid in preventing fragmentation if the clot enters the mouth of the catheter at an offset position.

The mechanical thrombectomy device will support the lumen of the vessel during aspiration such that it will be less likely to collapse under negative pressure and hold the clot together should the clot comprise an array of stiff and soft portions that may otherwise fragment. The mechanical thrombectomy device can also allow the user to pinch a clot that will not fully enter the lumen of the clot retrieval catheter, thereby ensuring that the clot will not dislodge from the clot retrieval catheter as the clot retrieval catheter, clot, and mechanical thrombectomy device are retracted as one through the vasculature, through the outer catheter, and outside of the patient. The interaction between the outer catheter and the expanded mouth will aid in gradually compressing the clot so that it can be pulled through the outer catheter with the clot retrieval catheter and mechanical thrombectomy device. If the clot is still too large to enter the outer catheter, the clot retrieval catheter and mechanical thrombectomy device can be retracted proximally through the vessel and into a second larger outer catheter such as a balloon guide. Should the clot still be too stiff to retrieve through the second outer catheter, all devices can be retracted together as one through the vasculature and outside of the body. The clot retrieval catheter may be designed to work with an outer catheter such as a 7Fr, 8Fr, 9Fr or 10Fr long guide sheath or balloon guide sheath. Alternatively, the clot retrieval catheter may be designed to work with an outer catheter such as a 4Fr, 5Fr, or 6Fr intermediate catheter.

FIG. 23 and FIG. 24 are flow diagrams each comprising method steps for producing a clot retrieval catheter having a support tube according to aspects of this disclosure. The method steps can be applied to any of the example systems, devices, and/or apparatus described herein or by a means that would be known to one of ordinary skill in the art.

Referring to a method 2300 outlined in FIG. 23, step 2310 describes the task of positioning a plurality of ribs along a length, the ribs being oriented circumferentially around a longitudinal axis to define a substantially tubular shaped support. The ribs can be circular, helical, or any other suitable shape appropriate for intravascular procedures. The ribs can be formed by laser cutting a hypotube, carving radial slots into an extruded tube, or other methods commonly known in the art. Step 2320 involves forming or positioning the plurality of ribs such that the flexibility of tubular support varies along at least part of the longitudinal length of the tubular support. For example, variable flexibility of the tubular support can be obtained by tuning various properties of the ribs, such as the spacing of the ribs, different thicknesses for the struts of the ribs, and adjusting the planar cross-sectional shape of the ribs. In step 2330, the plurality of ribs can be cut or formed at one or more angles which are not perpendicular to the longitudinal axis of the tubular support. As the tubular support is subjected to tensile or compressive loads during the thrombectomy procedure, the angled orientation of the ribs can change the cross-sectional size of the internal catheter lumen, facilitating clot retrieval and/or aspiration.

Step 2340 can involve forming one or more spines running along the length of the tubular support and can include affixing each rib of the plurality of ribs to the one or more spines. The spines can be mechanically connected to the ribs, or the spines and ribs can be formed integrally through the machining of a hypotube or the cutting of radial slots in an extruded tube. Having fixed junction or attachment points to the spine or spines allows the ribs to be configured to move proximally or distally with respect to the spine or spines when the tubular support is subjected to different forces during a procedure, as in step 2350. This movement can allow the tubular support to increase in diameter locally as a clot is being withdrawn, or reduce frictional forces generated with the clot retrieval catheter is advanced or retracted through an outer catheter. Different configurations of the ribs and spines of the tubular support can be appreciated to encourage movement of the ribs, such as narrowed ribs struts or when a single axial spine is used to give each rib an unconstrained free end.

Turing to method 2400 outlined in FIG. 24, in step 2410, the one or more spines of the tubular support are oriented to share the longitudinal axis of the support tube. For instance, straight axial spines can share an axis parallel to, or a helical spine arrangement can have twists concentric with, the longitudinal axis of the tubular support. In step 2420, the spines can also be cut or formed such that the flexibility of the tubular support varies along the length of the tubular support. A thicker proximal width of a spine can transition to a thinner width to maintain good trackability characteristics within vessels while giving distal portions of the tubular support greater flexibility for access.

A further step for preparing a tubular support for a clot retrieval catheter is shown in step 2430, which can involve fixedly attaching or integrally forming a radially-expanding tip with the distal end of the tubular support so that the catheter can have a large, distal facing mouth which can seal with the vessel and provide local flow restriction/arrest when deployed. In step 2440, at least a portion of the tubular support and expandable tip can be covered with a polymeric cover. A cover, for example, can be a series of outer jackets which are reflowed, injection molding, or laminated to the outer and/or inner radially surfaces of the ribs. One of skill in the art can also appreciate that a coating step can give the surfaces of the tubular support and/or cover lubricious, low-friction properties.

The invention is not necessarily limited to the examples described, which can be varied in construction and detail. The terms "distal" and "proximal" are used throughout the preceding description and are meant to refer to a positions and directions relative to a treating physician. As such, "distal" or distally" refer to a position distant to or a direction away from the physician. Similarly, "proximal" or "proximally" refer to a position near to or a direction towards the physician. Furthermore, the singular forms "a," "an," and "the" include plural referents unless the context clearly dictates otherwise.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

In describing example embodiments, terminology has been resorted to for the sake of clarity. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Some steps of a method can be performed in a different order than those described herein without departing from the scope of the disclosed technology. Similarly, it is also to be understood that the mention of one or more components in a device or system does not preclude the presence of additional components or intervening components between those components expressly identified. For clarity and conciseness, not all possible combinations have been listed, and such modifications are often apparent to those of skill in the art and are intended to be within the scope of the claims which follow.

What is claimed is:

1. A tube forming the body of a catheter assembly, the tube comprising:
   a tubular support framework comprising a proximal end, a distal end, and a longitudinal axis, the support framework comprising:
   one or more spines each being formed as a continuous spine disposed in a configuration parallel to the longitudinal axis and extending longitudinally between the proximal end and the distal end;
   a plurality of interlocking ribs disposed along a length of the one or more spines defining a lumen of the support framework extending therethrough;
   at least one radial slot adjacent each of the plurality of interlocking ribs; and
   a polymeric cover disposed around at least a portion of the support framework.

2. The tube of claim 1, wherein at least one of the one or more spines has a proximal spine width different from a distal spine width between the proximal end and the distal end of the support framework.

3. The tube of claim 1, wherein the widths of the radial slots vary between the proximal end and the distal end of the support framework.

4. The tube of claim 1, wherein ends of the radial slots are aligned along the length of the one or more spines.

5. The tube of claim 1, wherein at least one of the plurality of interlocking ribs has a first rib width different than a second rib width of another rib of the plurality of interlocking ribs.

6. The tube of claim 1, wherein the radial slots are configured for bending of the support framework.

7. The tube of claim 1, wherein the support framework is configured to bend or torque in multiple planes.

8. The tube of claim 1, wherein the radial slots form a puzzle-cut pattern.

9. A tube forming the body of a catheter assembly, the tube comprising:
- a tubular support framework comprising a proximal end, a distal end, an internal lumen, and a plurality of interlocking rings defining a pattern of radial slots configured around a longitudinal axis;
- one or more spines each being formed as a continuous spine disposed in a configuration parallel to the longitudinal axis and extending longitudinally between the proximal end and the distal end; and
- a polymeric cover disposed around at least a portion of the support framework.

10. The tube of claim 9, wherein the radial slots form a puzzle-cut pattern.

11. The tube of claim 9, wherein the interlocking rings are configured for bending of the support framework.

\* \* \* \* \*